United States Patent
Tah et al.

(10) Patent No.: US 10,105,153 B2
(45) Date of Patent: Oct. 23, 2018

(54) MULTIFUNCTION RETRIEVAL DEVICES AND RELATED METHODS

(71) Applicant: Boston Scientific Scimed, Inc., Maple Grove, MN (US)

(72) Inventors: Richard C. Tah, Framingham, MA (US); Jozef Slanda, Milford, MA (US); Ronald Ciulla, Westford, MA (US); Jianmin Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 328 days.

(21) Appl. No.: 14/521,599

(22) Filed: Oct. 23, 2014

(65) Prior Publication Data
US 2015/0119895 A1     Apr. 30, 2015

Related U.S. Application Data

(60) Provisional application No. 61/897,662, filed on Oct. 30, 2013.

(51) Int. Cl.
| A61B 17/22 | (2006.01) |
| A61B 17/221 | (2006.01) |
| A61B 17/00 | (2006.01) |

(52) U.S. Cl.
CPC ...... *A61B 17/221* (2013.01); *A61B 17/22031* (2013.01); *A61B 2017/00353* (2013.01); *A61B 2017/2212* (2013.01); *A61B 2017/2215* (2013.01)

(58) Field of Classification Search
CPC ...... A61B 17/221; A61B 17/22031–17/22032; A61B 2017/2212–2017/2217
See application file for complete search history.

(56) References Cited

U.S. PATENT DOCUMENTS

| 5,190,561 A * | 3/1993 | Graber ............. A61B 17/00234 606/114 |
| 6,010,512 A | 1/2000 | Chu et al. |
| 6,383,195 B1 * | 5/2002 | Richard ............... A61B 17/221 606/114 |
| 2005/0154378 A1 * | 7/2005 | Teague ................. A61B 17/221 606/2.5 |

FOREIGN PATENT DOCUMENTS

EP         0 997 108 B1     10/2008

* cited by examiner

*Primary Examiner* — Shaun L David
(74) *Attorney, Agent, or Firm* — Bookoff McAndrews, PLLC

(57) ABSTRACT

A device may include a handle, and a sheath coupled to the handle. The sheath may include a lumen. The device may also include an instrument assembly coupled to the handle, and extending through the lumen of the sheath. The instrument assembly may include a basket configured to move relative to the sheath, and between contracted and expanded states. The instrument assembly may also include a forceps configured to reciprocate along a central longitudinal axis of the basket and through an interior of the basket, and move between contracted and expanded states.

20 Claims, 14 Drawing Sheets

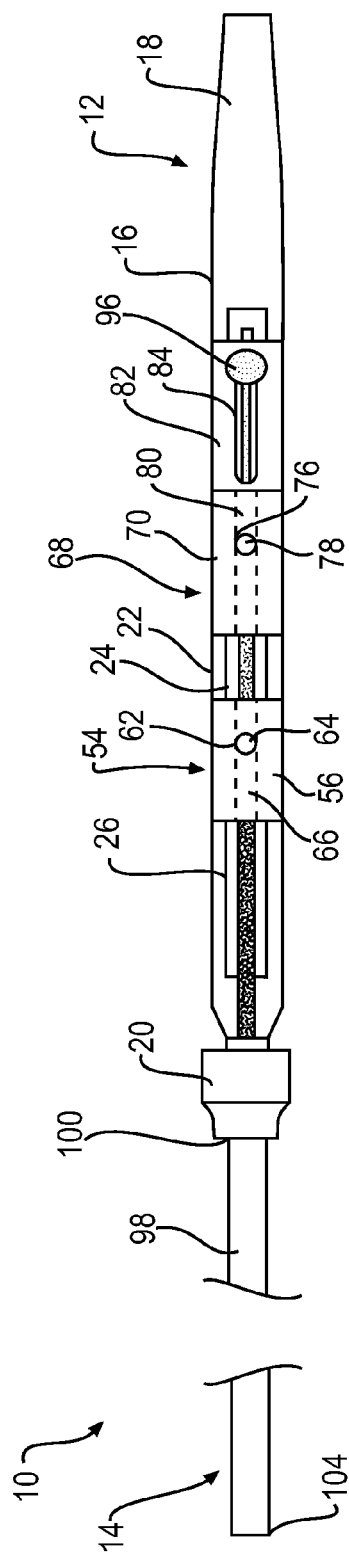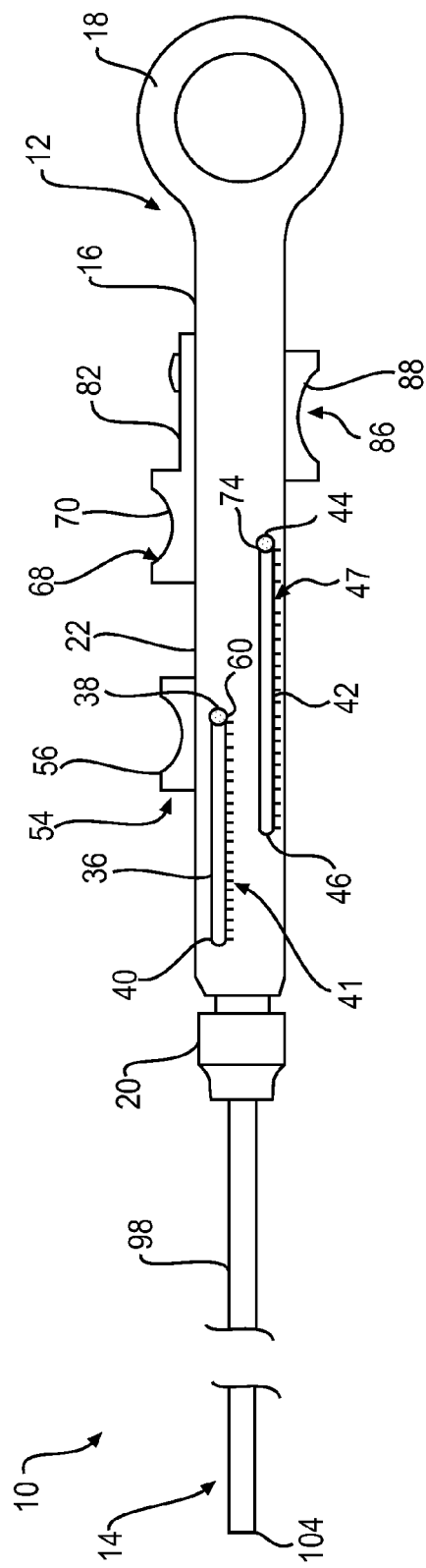
FIG. 1A
FIG. 1B

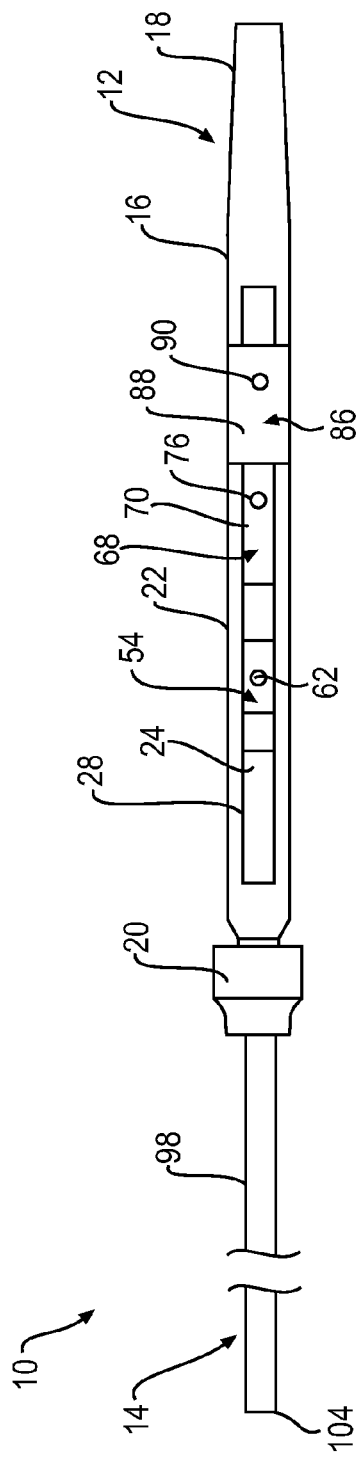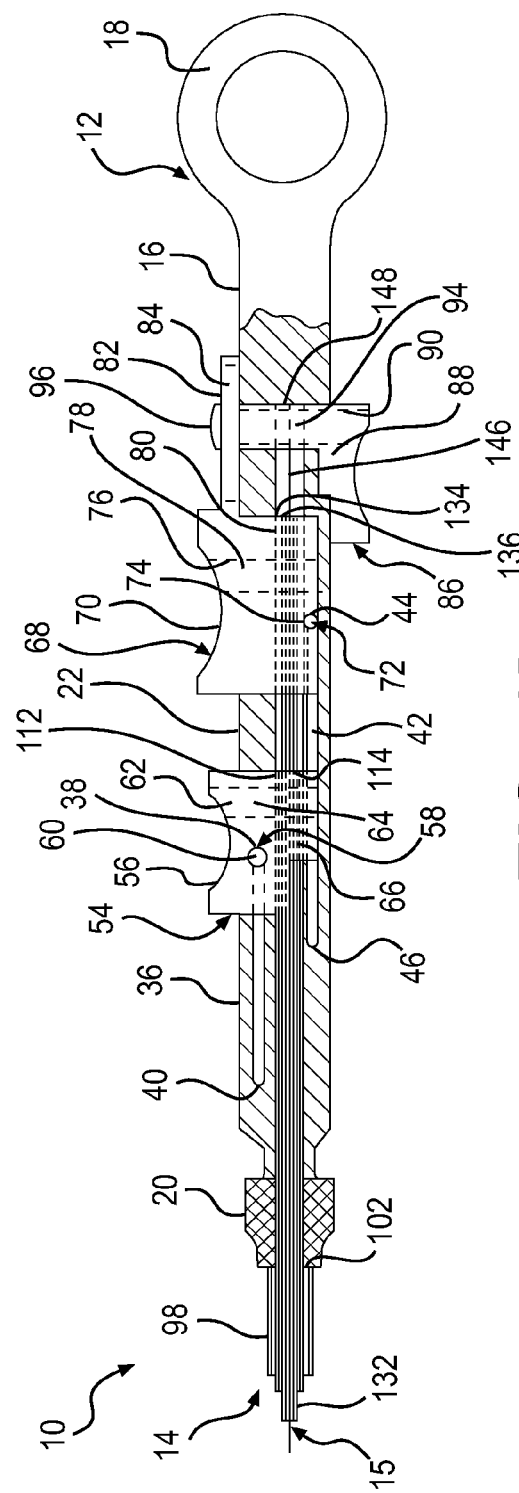

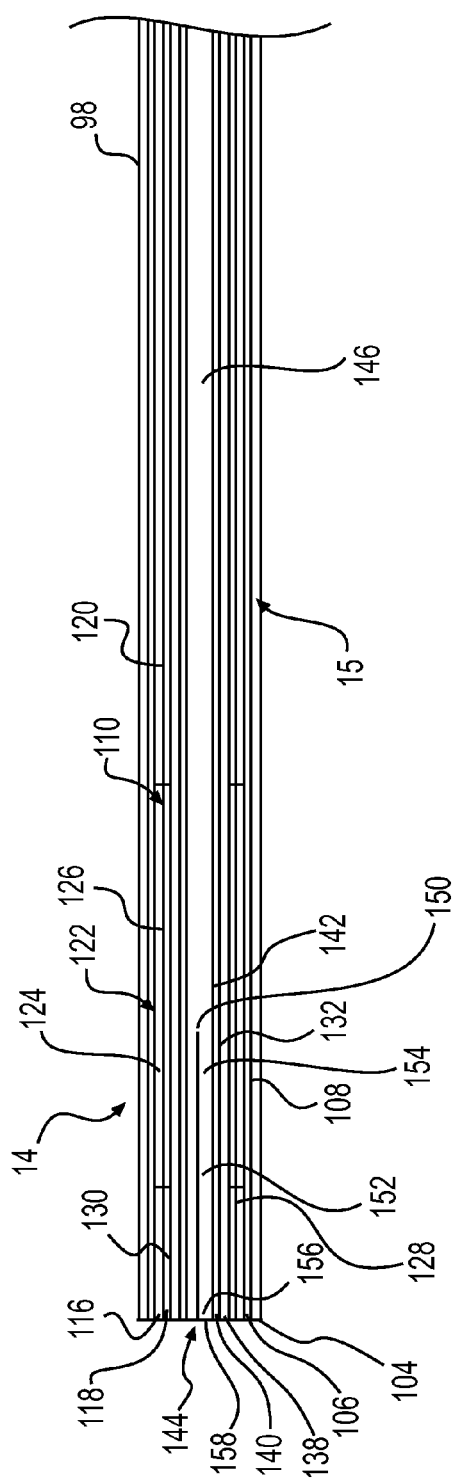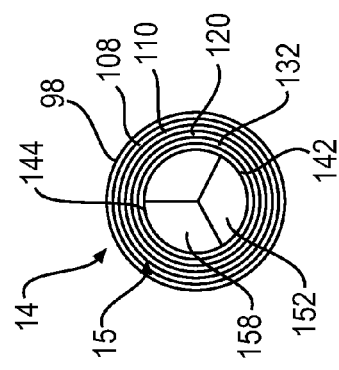
FIG. 2A
FIG. 2B

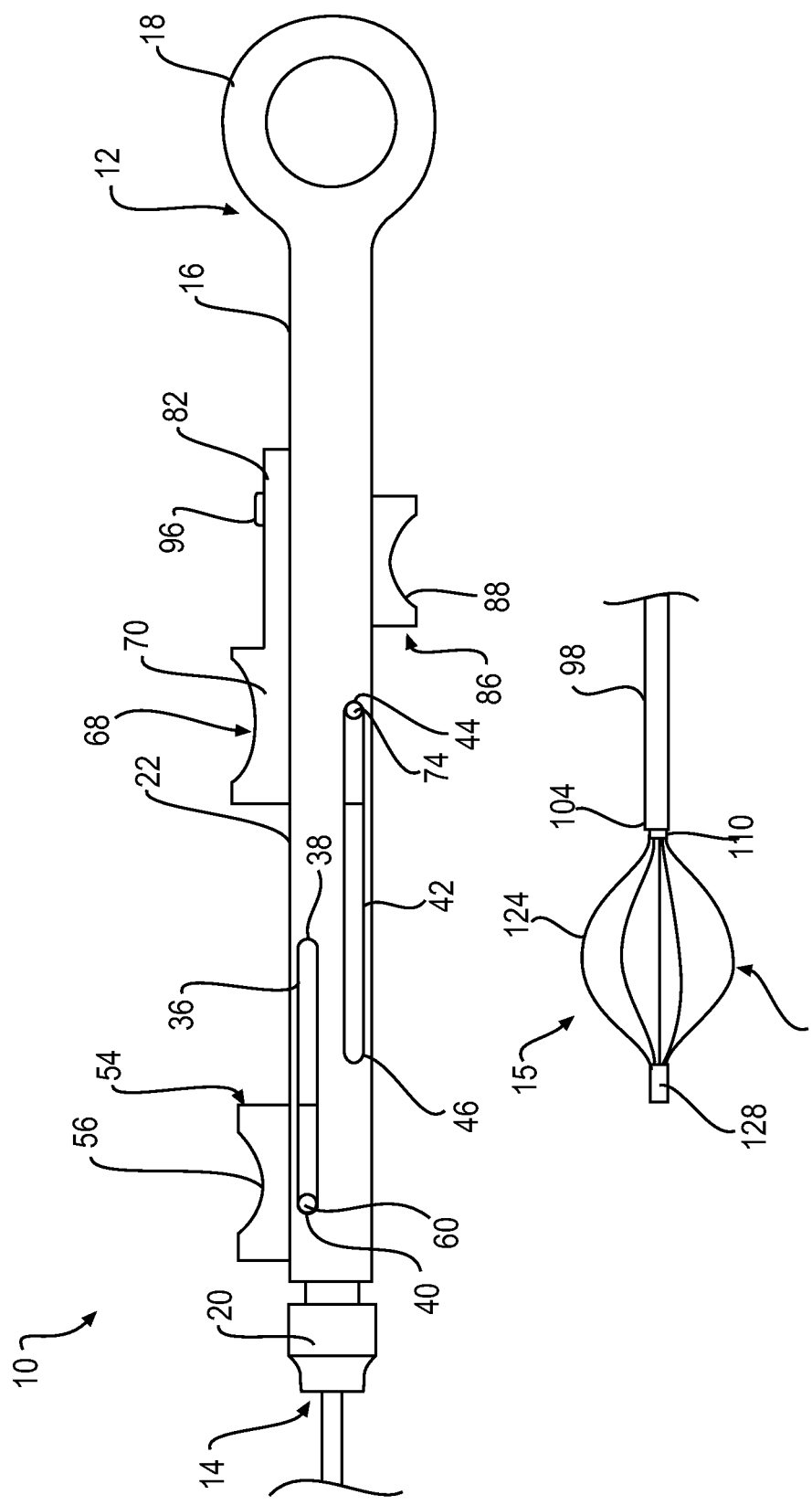

MULTIFUNCTION RETRIEVAL DEVICES AND RELATED METHODS

This application claims the benefit of U.S. Provisional Application No. 61/897,662, filed Oct. 30, 2013, the disclosure of which is incorporated herein by reference in its entirety.

TECHNICAL FIELD

Embodiments of the present disclosure relate generally to retrieval devices. In particular, embodiments of the present disclosure relate to multifunction retrieval devices, and procedures performed with the multifunction retrieval devices.

BACKGROUND

Retrieval devices may be used to retrieve objects, such as stones, from a subject's body. Commonly, such retrieval devices may include baskets or forceps for grasping objects. A basket may be introduced into a target area of a subject's body while in a contracted state, and may be expanded near an object targeted for retrieval. The expanded basket may be maneuvered to guide the object through a space between legs of the basket. For example, the expanded basket may be used to press the object against a wall of a body lumen, causing the object to force basket legs apart and thereby allowing the object to enter an interior region of the basket. In some instances, however, forcing the object against the wall may damage tissue at the point of contact.

In some instances, the presence of the object in the basket may cause the basket to remain at least partially expanded such that a diameter of the basket may exceed a diameter of a body lumen or opening at or near the target area. This may block withdrawal of the basket and the object from the subject. In such cases, release of the object from the basket may be a prerequisite for withdrawal of the basket from the subject. However, even if the basket is put in its expanded state, the object may be so large that it may not exit from the basket without intervention. Thus, additional procedures and/or devices may be required to free the object from the basket.

Grasping forceps also may be used to grasp objects in a subject's body. The forceps may include prongs that may be deployed to engage and grasp an object. The prongs may damage tissue near the site of the object. Even after the object is captured, the object may be pulled or pushed out of the forceps during withdrawal of the forceps from the subject's body.

Therefore, it may be useful to provide devices with enhanced capabilities, thereby providing ease of retrieval and/or release of an object from within a retrieval assembly.

SUMMARY OF THE DISCLOSURE

According to an aspect of the present disclosure, a device may include a handle, and a sheath coupled to the handle. The sheath may include a lumen. The device may also include an instrument assembly coupled to the handle, and extending through the lumen of the sheath. The instrument assembly may include a basket configured to move relative to the sheath, and between contracted and expanded states. The instrument assembly may also include a forceps configured to reciprocate along a central longitudinal axis of the basket and through an interior of the basket, and move between contracted and expanded states.

Various embodiments of the device may include one or more of the following features: the forceps may be configured to pass through the basket while the basket is expanded; the forceps may be configured to pass through the basket while the basket is contracted; in the contracted state of the basket, the basket may include a lumen configured to slidably receive the forceps; a central longitudinal axis of the forceps may be coaxial with the central longitudinal axis of the basket when the basket is contracted; the instrument assembly may include a forceps sheath, the forceps sheath including a forceps lumen configured to slidably receive a forceps; the forceps may be extendable distally beyond a distal end of the basket; the forceps may be selectively retractable into and extendable out of the forceps lumen; and/or the basket may be at a distal portion of a basket sheath, the basket sheath including a forceps sheath lumen configured to slidably receive the forceps sheath.

According to another aspect of the present disclosure, a device may include a handle, and a first sheath coupled to the handle. The first sheath may include a first lumen. The device may also include an instrument assembly coupled to the handle. The instrument assembly may include a second sheath coupled to the handle and extending through the first lumen. The second sheath may include a second lumen. The instrument assembly may also include a basket coupled to an end of the second sheath. The basket may be configured to move relative to the first sheath, and between contracted and expanded states. The instrument assembly may also include a third sheath coupled to the handle and extending through the second lumen. The third sheath may include a third lumen. The third sheath may be configured to move relative to the second sheath, and between retracted and extended states. The instrument assembly may also include a forceps coupled to the handle and extending through the third lumen. The forceps may be configured to move relative to the third sheath, and between contracted and expanded states.

Various embodiments of the device may include one or more of the following features: the first sheath may include a distal end opening, and the basket may move through the end opening when moving between the contracted and expanded states of the basket; longitudinal axes of portions of the first sheath, second sheath, third sheath, and forceps may be coaxial; the forceps may include a proximal shaft and a plurality of distal arms; the handle assembly may include a housing, and a first slidable member configured to slide relative to the housing, a proximal portion of the second sheath being coupled to the first slidable member; the handle assembly may include a second slidable member configured to slide relative to the housing, a proximal portion of the third sheath being coupled to the second slidable member; the handle assembly may include a third slidable member configured to slide relative to the housing, a proximal portion of the forceps being coupled to the third slidable member; and/or the second slidable member may be configured to selectively engage the with the third slidable member.

According to yet another aspect of the present disclosure, a method for handling an object in a target area of the body of a subject may include positioning a distal end of a device at the target area. The device may include a handle, and a sheath coupled to the handle. The sheath may include a lumen. The device may also include an instrument assembly coupled to the handle, and extending through the lumen of the sheath. The instrument assembly may include a basket configured to move relative to the sheath and between contracted and expanded states. The instrument assembly may also include a forceps configured to reciprocate along a central longitudinal axis of the basket and through an interior of the basket, and move between contracted and expanded states. The method may also include entrapping the object in an interior of the basket.

Various embodiments of the method may include one or more of the following features: entrapping the object in an interior of the basket may include extending the forceps beyond a distal end of the basket to grasp the object, and retracting the forceps to draw the object into the interior of the basket; and/or extending the forceps to force the object back out of the interior of the basket, and releasing the forceps from the object outside of the basket.

BRIEF DESCRIPTION OF THE DRAWINGS

The accompanying drawings, which are incorporated herein and constitute a part of this specification, illustrate exemplary embodiments of the present disclosure and, together with the description, serve to explain the principles of the disclosure.

FIG. 1A is a top view of an exemplary device, according to aspects of the present disclosure.

FIG. 1B is a side view of the device of FIG. 1A, according to aspects of the present disclosure.

FIG. 1C is a bottom view of the device of FIG. 1A, according to aspects of the present disclosure.

FIG. 1D is a cross-sectional side view of the device of FIG. 1A, according to aspects of the present disclosure.

FIG. 2A is a cross-sectional side view of an embodiment of a distal portion of the device of FIG. 1A, according to aspects of the present disclosure.

FIG. 2B is an end view of the embodiment of the distal portion of the device of FIG. 2A, according to aspects of the present disclosure.

FIGS. 3A to 3F illustrate the device of FIG. 1A in various states of operation, according to aspects of the present disclosure.

DESCRIPTION OF THE EMBODIMENTS

Reference will now be made in detail to embodiments of the present disclosure, examples of which are illustrated in the accompanying drawings. Wherever possible, the same reference numbers will be used throughout the drawings to refer to the same or like parts. The term "distal" refers to a portion farthest away from a user when introducing a device into a subject. By contrast, the term "proximal" refers to a portion closest to the user when placing the device into the subject.

Figure 3A:
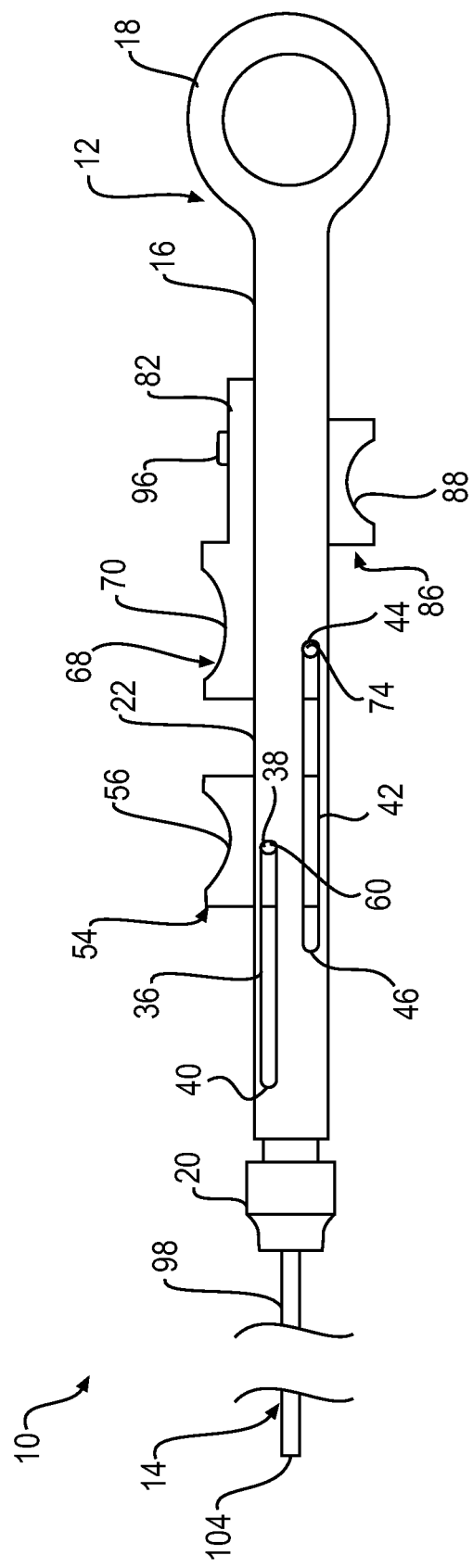

FIGS. 1A-1D show multiple views of an exemplary device 10, according to aspects of the present disclosure. The device 10 may include a proximal handle assembly 12, a sheath assembly 14, and an instrument assembly 15 (FIG. 3E). The handle assembly 12 may include a handle housing 16 configured to house and/or support one or more components of the handle assembly 12. The handle housing 16 may be designed for ease of use and ergonomics. The handle assembly 12 may be coupled to the sheath assembly 14 by a coupling element 20. The coupling element 20 may be configured to receive the sheath assembly 14 at a distal end, and the handle assembly 12 at a proximal end. The coupling element 20 may be hollow to provide a passage for components extending distally out of the handle assembly 12.

The handle housing 16 may include a main body 22 with a gripping member 18 on a proximal end. The gripping member 18 may include a loop, handle, grip, and/or other suitable contours that may be easily grasped and handled by a user. The proximal gripping member 18 may be made of a variety of materials including, but not limited to, polymers, metals, and/or metal alloys. Additionally, the proximal gripping member 18 may be coated with high friction or non-slip material, such as, for example, a soft rubber or rubber-like material (e.g., Sorbathane® material), a thermoplastic elastomer (TPE) material, a gel material, or the like. Additionally or alternatively, the gripping member 18 may include one or more protrusions or indentations on its outer surface, to facilitate handling of the device 10.

The main body 22 may include a central passage 24 extending longitudinally therethrough. The main body 22 may include slots 26, 28, 36, and 42 opening into the central passage 24. For example, the main body 22 may include the top slot 26 (FIG. 1A) on a top surface. The top slot 26 may receive portions of a first button unit 54 and a second button unit 68. Top portions of the first and second button units 54 and 68 may protrude from the main body 22, while bottom portions of the first and second button units 54 and 68 may extend through the top slot 26 into the central passage 24 of the main body 22. Side portions of the first and second button units 54 and 68 may extend over side portions of the main body 22 surrounding the top slot 26.

The first button unit 54 may include a first button 56 configured to slide reciprocally (e.g., proximally and distally) along the top slot 26, and relative to the main body 22. The first button 56 may include a vertical passage 62 for receiving a holding member 64, which may be, for example, a screw, pin, adhesive, or any other suitable fastener. The first button 56 may also include a horizontal passage 66. The horizontal passage 66 may be configured to receive a basket sheath 110, forceps sheath 132, and forceps 144 of the instrument assembly 15. The first button 56 may also include a lateral passage 58 (FIG. 1D) configured to receive a dowel pin 60. Each of the vertical passage 62, horizontal passage 66, and lateral passage 58 may be disposed at an angle (e.g., perpendicularly) to the other two passages. The vertical passage 62 may open into the horizontal passage 66.

The second button unit 68 may include a second button 70 configured to slide reciprocally (e.g., proximally and distally) along the top slot 26, and relative to the main body 22. The second button 70 may include a vertical passage 76 for receiving a holding member 78, which may be, for example, a screw, pin, adhesive, or any other suitable fastener. The second button 70 may also include a horizontal passage 80. The horizontal passage 80 may be configured to receive the forceps sheath 132 and forceps 144 of the instrument assembly 15. The second button 70 may also include a lateral passage 72 configured to receive a dowel pin 74. Each of the lateral passage 72, vertical passage 76, and horizontal passage 80 may be disposed at an angle (e.g., perpendicularly) to the other two passages. The vertical passage 76 may open into the horizontal passage 80. The second button 70 may also include an extension 82. The extension 82 may extend proximally and may include a slot 84 (FIGS. 1A and 1D) extending between its top and bottom surfaces. The slot 84 may slidably receive a pin or screw 96 of a third button unit 86 (FIGS. 1B and 1D).

The main body 22 may include a bottom slot 28 (FIG. 1C), which may slidably receive a portion of the third button unit 86. An upper portion of the third button unit 86 may extend through the bottom slot 28 and into the central passage 24, while a bottom portion of the third button unit 86 may protrude from the main body 22. The third button unit 86 may include a third button 88 configured to slide reciprocally (e.g., proximally and distally) along the bottom slot 28, and relative to the main body 22. The third button 88 may include a vertical passage 90 for receiving the screw 96. The third button 88 may also include a horizontal passage 94, which may be configured to receive the forceps 144 of the instrument assembly 15. The vertical passage 90 may open into the horizontal passage 94. The third button 88 may be slidably coupled to the second button 70 via passage of the screw 96 through the slot 84.

The main body 22 may include at least one upper side slot 36 and at least one lower side slot 42 (FIGS. 1B, 1D, 3A-3F, 4, and 7). The upper side slot 36 may have a proximal end 38 and a distal end 40. The lower side slot 42 may have a proximal end 44 and a distal end 46. While one upper side slot 36 is shown, it should be understood that the upper side slot 36 may be one of a pair of upper side slots on opposite sides of the main body 22. The lower side slot 42 may also be one of a pair of lower side slots on opposite sides of the main body 22.

At least one end of the dowel pin 60 of the first button unit 54 may be slidably received within the upper side slot 36. As the first button 56 is moved, the dowel pin 60 may slide along the upper side slot 36. The proximal and distal ends 38 and 40 of the upper side slot 36 may restrict movement of the dowel pin 60.

At least one end of the dowel pin 74 of the second button unit 68 may be slidably received within the lower side slot 42. As the second button 70 is moved, the dowel pin 74 may slide along the lower side slot 42. The proximal and distal ends 44 and 46 of the lower side slot 42 may restrict movement of the dowel pin 74.

The screw 96 of the third button unit 86 may slide reciprocally (e.g., proximally and distally) along the slot 84 of the second button unit 68. The screw 96 may, at times, come into contact with the proximal and distal ends of the slot 84. When the screw 96 is in contact with the proximal end of the slot 84, distal movement of the second button unit 68 (and the slot 84 therein) may force the screw 96 and the third button 88 to move in the distal direction. When the screw 96 is in contact with the distal end of the slot 84, proximal movement of the second button unit 68 may force the screw 96 and the third button unit 86 in the proximal direction. It is contemplated that any suitable protrusion and opening/cavity may be used in place of the screw 96 and the slot 84. It should be understood that any suitable lost motion connection may be provided to link the second button 70 and third button 88.

As shown in FIG. 1B, unit markings 41 and 47 may be placed alongside the upper side and lower side slots 36 and 42. The unit markings 41 and 47 may be used to gauge the positions of the pins 60 and 74, and thus the positions of the first and second buttons 56 and 70, relative to the handle housing 16. Although the unit markings 41 and 47 are shown along the upper and lower side slots 36 and 42 in some of the figures, it should be understood that such markings may be made at other suitable locations on the device 10. For example, unit markings also may be provided alongside the top slot 26 and/or the bottom slot 28.

The sheath assembly 14 may include an outer sheath 98. The outer sheath 98 may include a proximal end 100 coupled to the distal coupling element 20. The proximal end 100 may have a proximal opening 102 (FIG. 1D). A distal end 104 of the outer sheath 98 may have a distal opening 106 (FIG. 2A). The outer sheath 98 may include a lumen 108 extending between the proximal and distal openings 102 and 106. The lumen 108 may be in communication with the central passage 24 of the main body 22 via the coupling element 20.

The outer sheath 98 may receive the basket sheath 110 of the instrument assembly 15. The basket sheath 110 may have a proximal end 112 coupled to the first button unit 54. For example, the basket sheath 110 may be coupled to the first button 56 by being clamped or otherwise mechanically secured between surfaces of the first button 56 and the holding member 64. Alternatively, the proximal end 112 of the basket sheath 110 may be joined to the first button unit 56 using any suitable attachment mechanism such as adhesive or a melted attachment. The proximal end 112 may include a proximal opening 114 in communication with the horizontal passage 66 of the first button 56. The basket sheath 110 may be reciprocally slidable within the handle housing 16 and the outer sheath 98. For example, when the first button unit 54 is moved proximally, the basket sheath 110 may slide proximally within and relative to the handle housing 16 and the outer sheath 98. When the first button 56 is moved distally, the basket sheath 110 may slide distally within and relative to the handle housing 16 and outer sheath 98. The basket sheath 110 may have a distal end 116 and a distal opening 118. At least a portion of the distal end 116 may extend out from the distal end 104 of the outer sheath 98 when the basket sheath 110 is moved distally relative to the outer sheath 98. The basket sheath 110 may also include a lumen 120 extending from its proximal opening 114 to its distal opening 118.

The distal portion of the basket sheath 110 may include a basket 122 (FIGS. 3B and 3E). The basket 122 may move between a contracted state (FIG. 2A), where the basket 122 is restrained by the outer sheath 98, and an expanded state (FIGS. 3B and 3E), where the basket 122 is extended out of the outer sheath 98. The basket 122 may include legs or struts 124 (FIGS. 3B and 3E). The struts 124 may be inherently biased to move toward the expanded state in the absence of a restraining force keeping them in the contracted state. The struts 124 may form walls surrounding a lumen portion 126 (FIG. 2A) when the basket 122 is in the contracted state. Any suitable number of struts 124 may be used. For example, fewer struts 124 may be used when retrieving larger objects, and more struts 124 may be used when retrieving smaller objects. A distal end of the basket 122 may include an endcap 128 (FIGS. 2A, 2B, 3B, and 3E) coupled to the struts 124. The endcap 128 may include a lumen portion 130 (FIGS. 2A, 2B, 3B, and 3E). The lumen portions 126 and 130 may form part of the lumen 120 through the basket sheath 110.

The basket sheath 110 may slidably receive a forceps sheath 132 (FIG. 1D) of the instrument assembly 15. The forceps sheath 132 may have a proximal end 134, coupled to the second button unit 68. For example, the forceps sheath 132 may be coupled to the second button unit 68 by being clamped between surfaces of the holding member 78 and the second button 70. Alternatively, the proximal end 134 of the forceps sheath 132 may be joined to the second button 70 using any suitable attachment mechanism such as an adhesive or by melting/melted attachment. The proximal end 134 may have a proximal opening 136 in communication with the horizontal passage 80 within the second button 70. The forceps sheath 132 may be reciprocally slidable within and relative to the handle housing 16 and the basket sheath 110. For example, when the second button 70 is moved proximally, the forceps sheath 132 may slide proximally within and relative to the handle housing 16 and the basket sheath 110. When the second button 70 is moved distally, the forceps sheath 132 may slide distally within and relative to the handle housing 16 and the basket sheath 110. The forceps sheath 132 may have a distal end 138 and a distal opening 140. At least a portion of the distal end 138 may extend out from the distal end 116 of the basket sheath 110 when the forceps sheath 132 is moved distally relative to the basket sheath 110.

The forceps sheath 132 may slidably receive a forceps 144 in its lumen 142. The forceps 144 may form part of the instrument assembly 15. The forceps 144 may include a proximal shaft 146. The shaft 146 may have a proximal end 148, coupled to the third button unit 86. For example, the proximal shaft 146 may be coupled to the third button 88 by clamping of the proximal shaft 146 by surfaces of the screw 96 and the third button 88. Alternatively, the proximal shaft 146 may be joined to the third button 88 using any suitable attachment mechanism such as an adhesive or by melting/melted attachment. Distal arms 152 (FIG. 3C) may be provided at a distal end 150 of the proximal shaft 146. Each of the arms 152 may include a proximal end 154, distal end 156, and distal tip 158.

The forceps 144 may be slidable reciprocally (e.g., proximally and distally) relative to and within the handle housing 16 and the forceps sheath 132. For example, when the third button unit 86 is moved proximally, the forceps 144 may slide proximally relative to and within the handle housing 16 and the forceps sheath 132. When the third button 88 is moved distally, the forceps 144 may slide distally relative to and within the handle housing 16 and the forceps sheath 132. At least a portion of the arms 152 may extend out from the distal end 138 of the forceps sheath 132 when the forceps 144 is moved distally relative to the forceps sheath 132. It is also contemplated that the forceps 144 and forceps sheath 132 may move together when engagement between the screw 96 of the third button unit 86 and ends of the slot 84 of the second button unit 68 links movement of the second and third button units 68 and 86. For example, the forceps 144 and forceps sheath 132 may move together with the forceps 144 enclosed within the forceps sheath 132, and/or with the forceps 144 extending out from the forceps sheath 132.

Figure 2C:
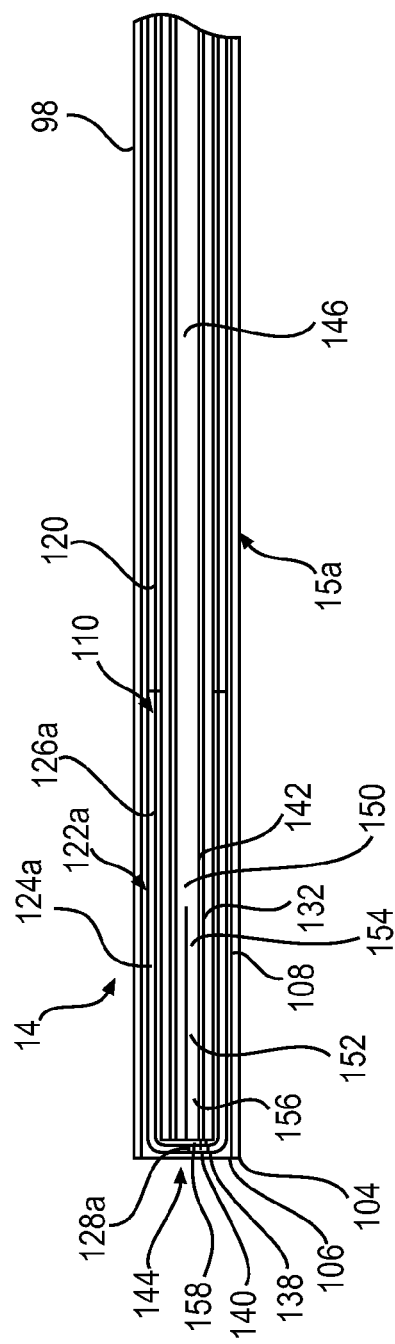
FIG. 2C is a cross-sectional side view of another embodiment of the distal portion of the device of FIG. 1A, according to aspects of the present disclosure.
Figure 3C:
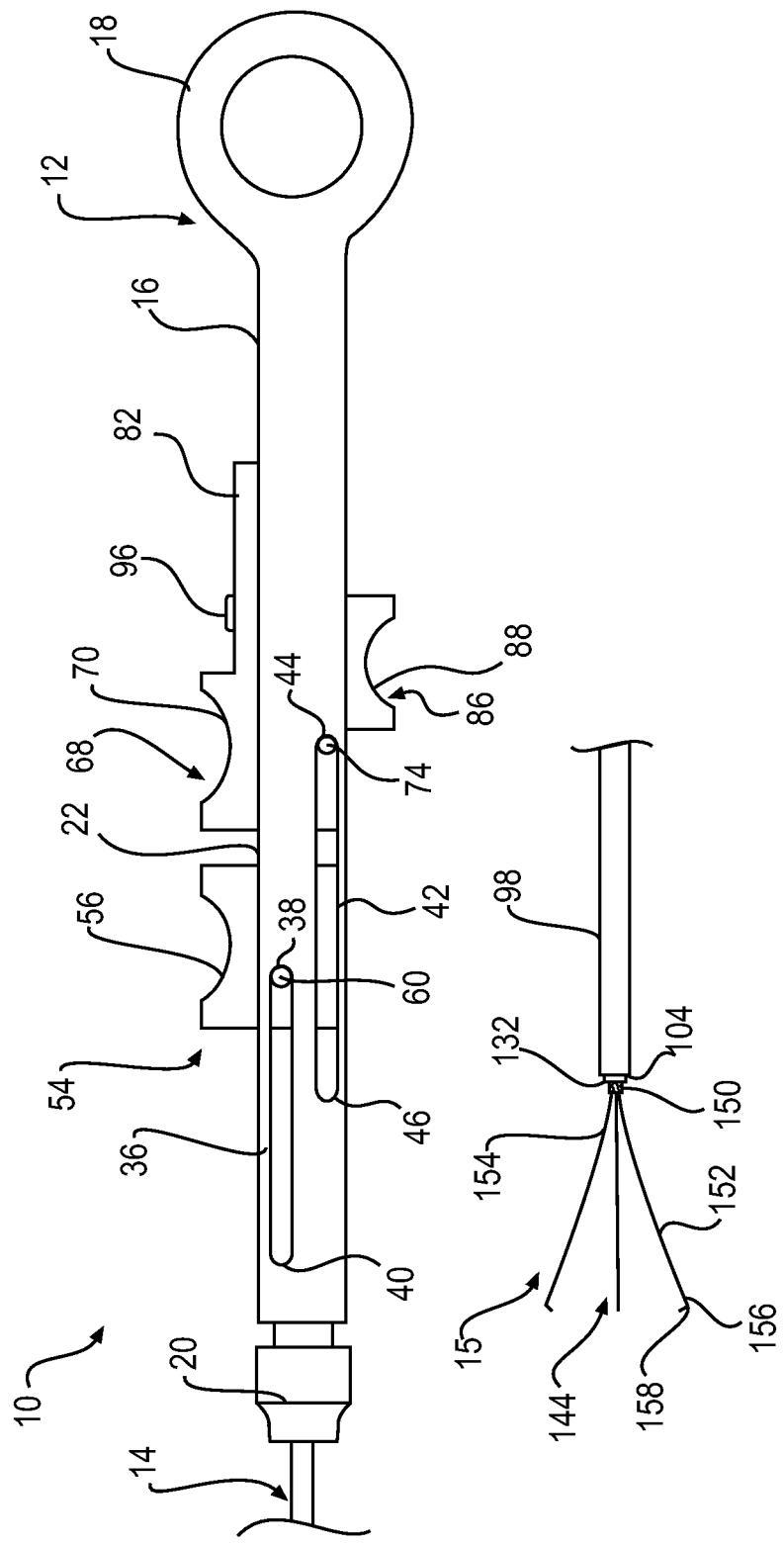
Figure 3D:
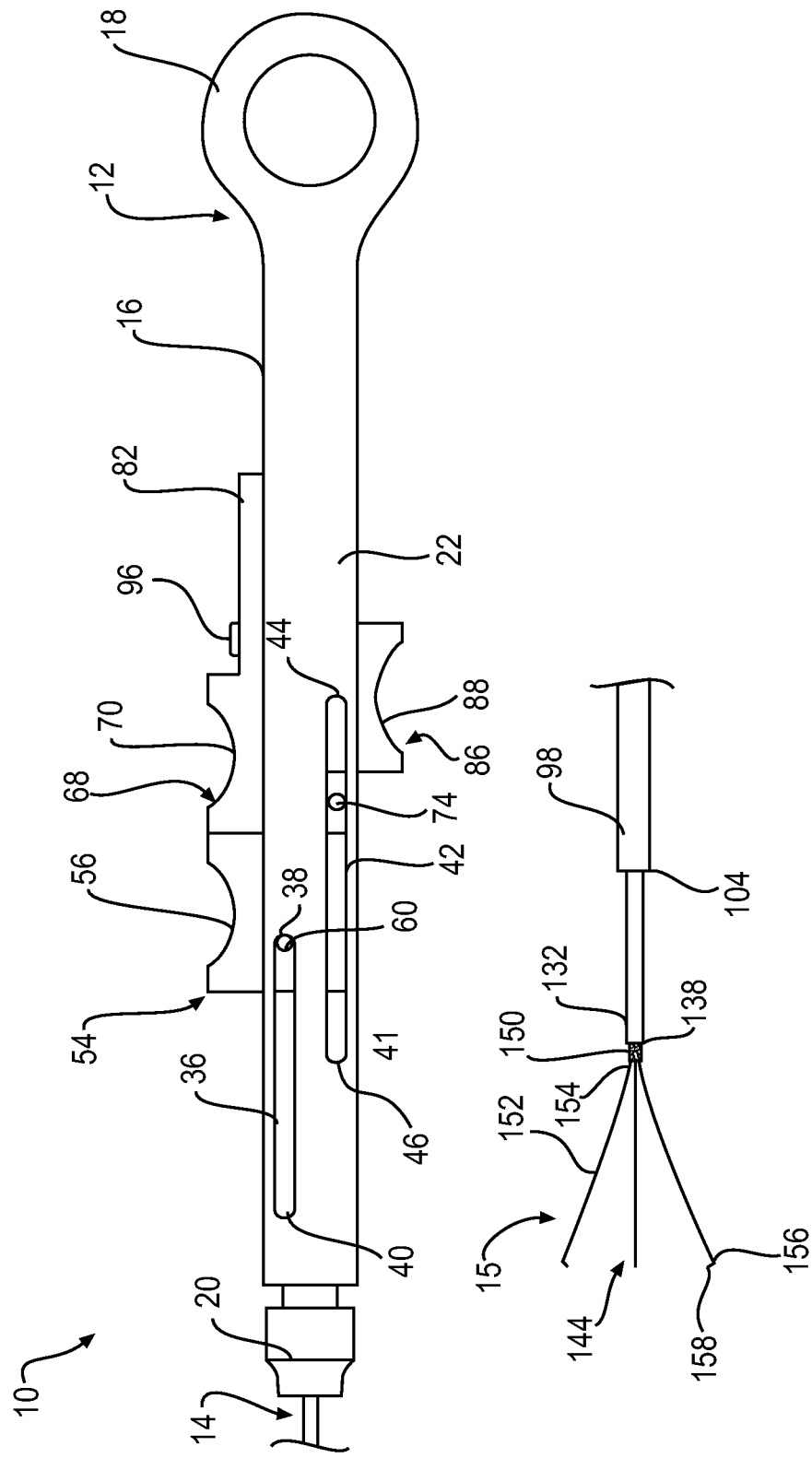
Figure 3E:
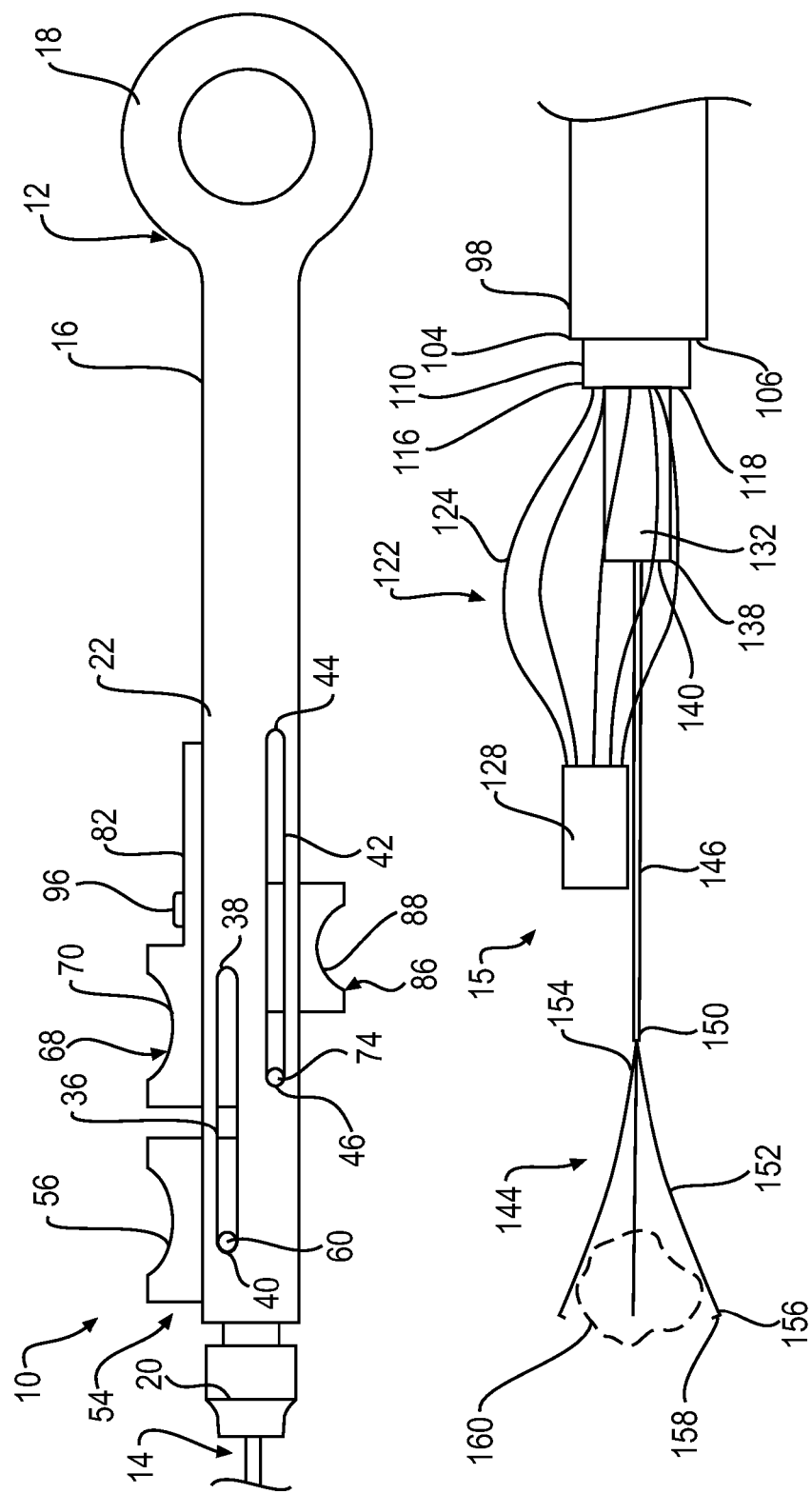

The distal arms 152 may have a contracted state (FIGS. 2A and 2B), and an expanded state (FIGS. 3C-3E). The distal arms 152 may be inherently biased to expand radially outwardly to the expanded state in the absence of a restraining force. The forceps sheath 132 may provide the restraining force to keep the distal arms 152 in the contracted state when the distal arms 152 are within the lumen 142. When the distal arms 152 protrude from the distal end 138 of the forceps sheath 132, they may expand radially outwardly.

As shown in FIG. 2A, at least a portion of the forceps 144 may extend through the basket sheath 110, including through the collapsed basket 122 and the endcap 128. The longitudinal axes of the basket sheath 110, forceps sheath 132, and forceps 144 may be coaxial in this state. When the forceps sheath 132 and forceps 144 are freed from the lumen 130 of the endcap 128, the longitudinal axes of the forceps sheath 132 and forceps 144 may be parallel to or angled relative to the longitudinal axis of the basket sheath 110.

The basket 122 and the forceps 144 may be made of a super elastic, elastic, or shape memory alloy such as Nitinol or any other suitable material. It should be understood that in addition to the basket 122 and the forceps 144, the device 10 may additionally include other end-effectors such as, but not limited to, morcellators, needles, hooks, forceps, energy delivery mechanisms, guide wires, scissors, and balloons. It is also contemplated that the struts 124 and/or the arms 152 may be electrodes configured to conduct electrical energy, such as radiofrequency energy. In such an embodiment, the basket sheath 110, forceps sheath 132, and/or forceps 144 may include one or more electrical conductors coupled to an electrical energy source in or coupled to the handle assembly 12.

Figure 2D:
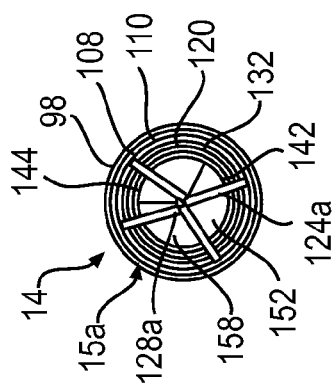
FIG. 2D is an end view of the embodiment of the distal portion of the device of FIG. 2C, according to aspects of the present disclosure.
Figure 3F:
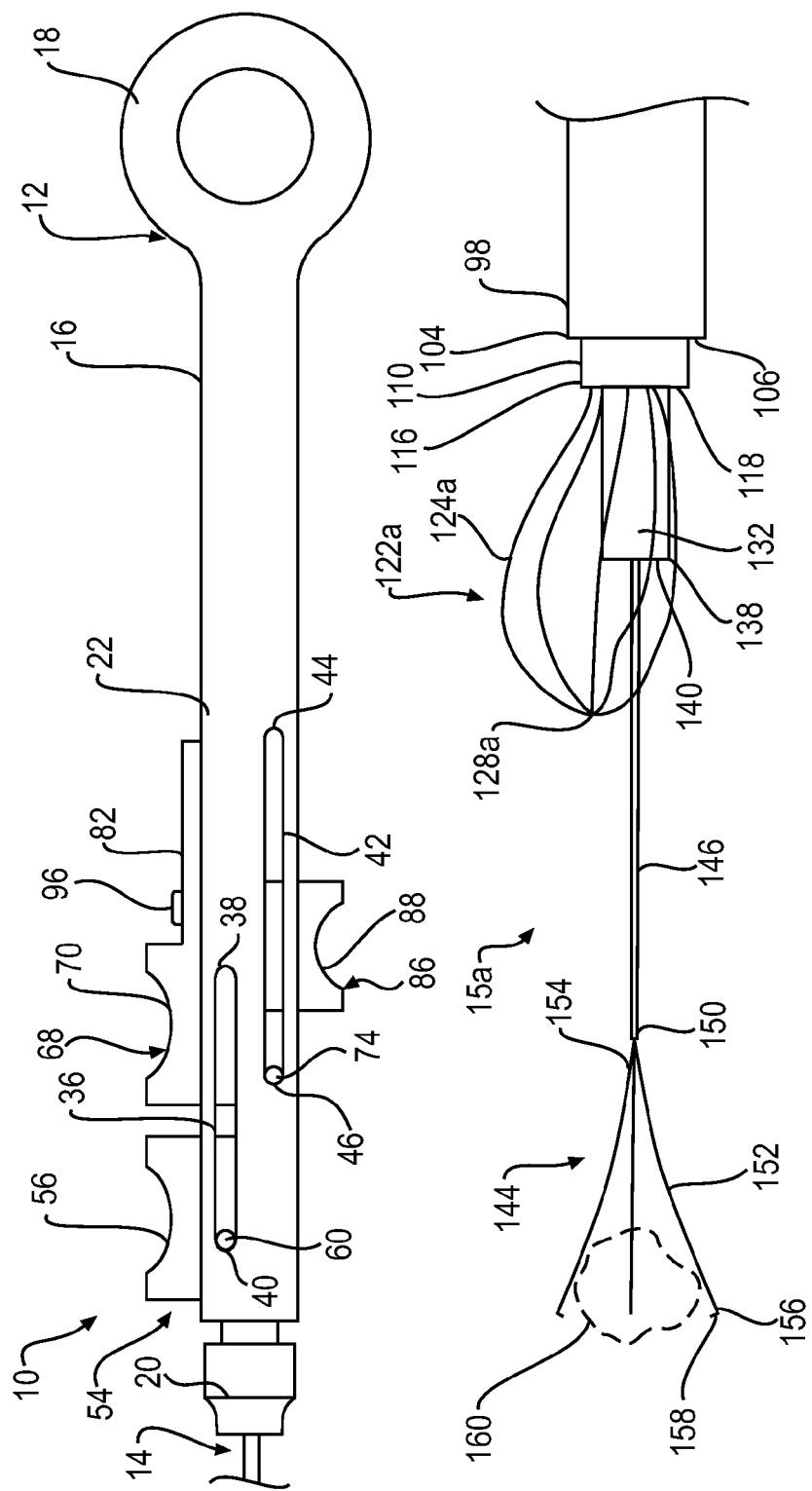

An alternative embodiment of the distal portion of the device 10 is shown in FIGS. 2C and 2D. In this embodiment, the distal portion of the basket sheath 110 may be coupled to a basket 122a. The basket 122a may move between a contracted state (as shown in FIGS. 2C and 2D), and an expanded state (as shown in FIG. 3F) where the basket 122a is extended out of the outer sheath 98. The basket 122a may include legs or struts 124a. The struts 124a may be inherently biased to move toward the expanded state in the absence of a restraining force keeping them in the contracted state. The struts 124a may form sides of a lumen portion 126a when the basket 122a is in the contracted state. Any suitable number of struts 124a may be used. A distal end of the basket 122a may include a tip 128a. The tip 128a may include distal ends of the struts 124a. For example, the tip 128a may include one or more knots formed by distal ends of the struts 124a, the one or more knots coupling the distal ends of the struts 124a. Additionally or alternatively, it is contemplated that the struts 124a may be bent, welded, pinned, rolled, or joined by any other suitable mechanical coupling at the tip 128a.

Portions of the forceps sheath 132 and forceps 144 may extend through the basket sheath 110. Portions of the forceps sheath 132 and forceps 144 may extend through the basket 122a. The longitudinal axes of the basket sheath 110 and/or basket 122a, forceps sheath 132, and forceps 144 may be coaxial in this state. When the forceps sheath 132 and forceps 144 are freed from the confines of the basket 122a, the longitudinal axes of the forceps sheath 132 and forceps 144 may be parallel to or angled relative to the longitudinal axis of the basket 122a and/or basket sheath 110.

The basket 122a may be made of a super elastic, elastic, or shape memory alloy such as nitinol or any other suitable material. It is also contemplated that the struts 124a may be electrodes configured to conduct electrical energy, such as radiofrequency energy. In such an embodiment, the basket sheath 110, forceps sheath 132, and/or forceps 144 may include one or more electrical conductors coupled to an electrical energy source in or coupled to the handle assembly 12.

Figure 4:
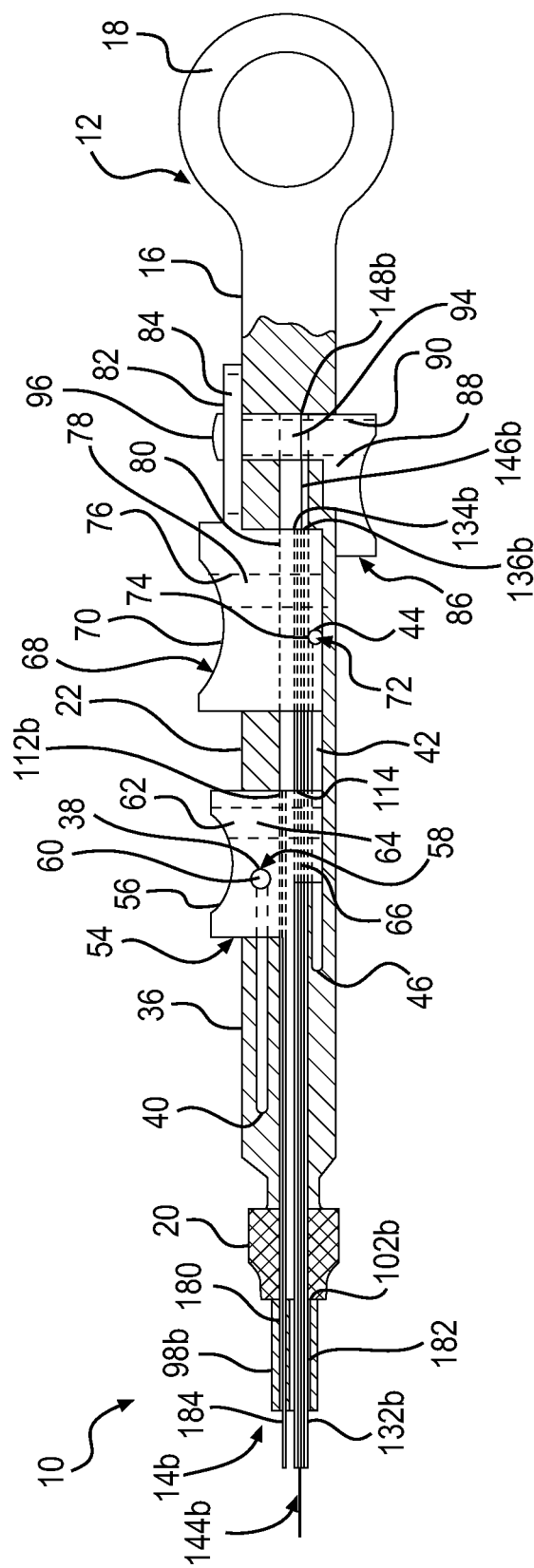
FIG. 4 is a cross-sectional side view of an alternative embodiment of the device of FIG. 1A, according to aspects of the present disclosure.
Figure 5:
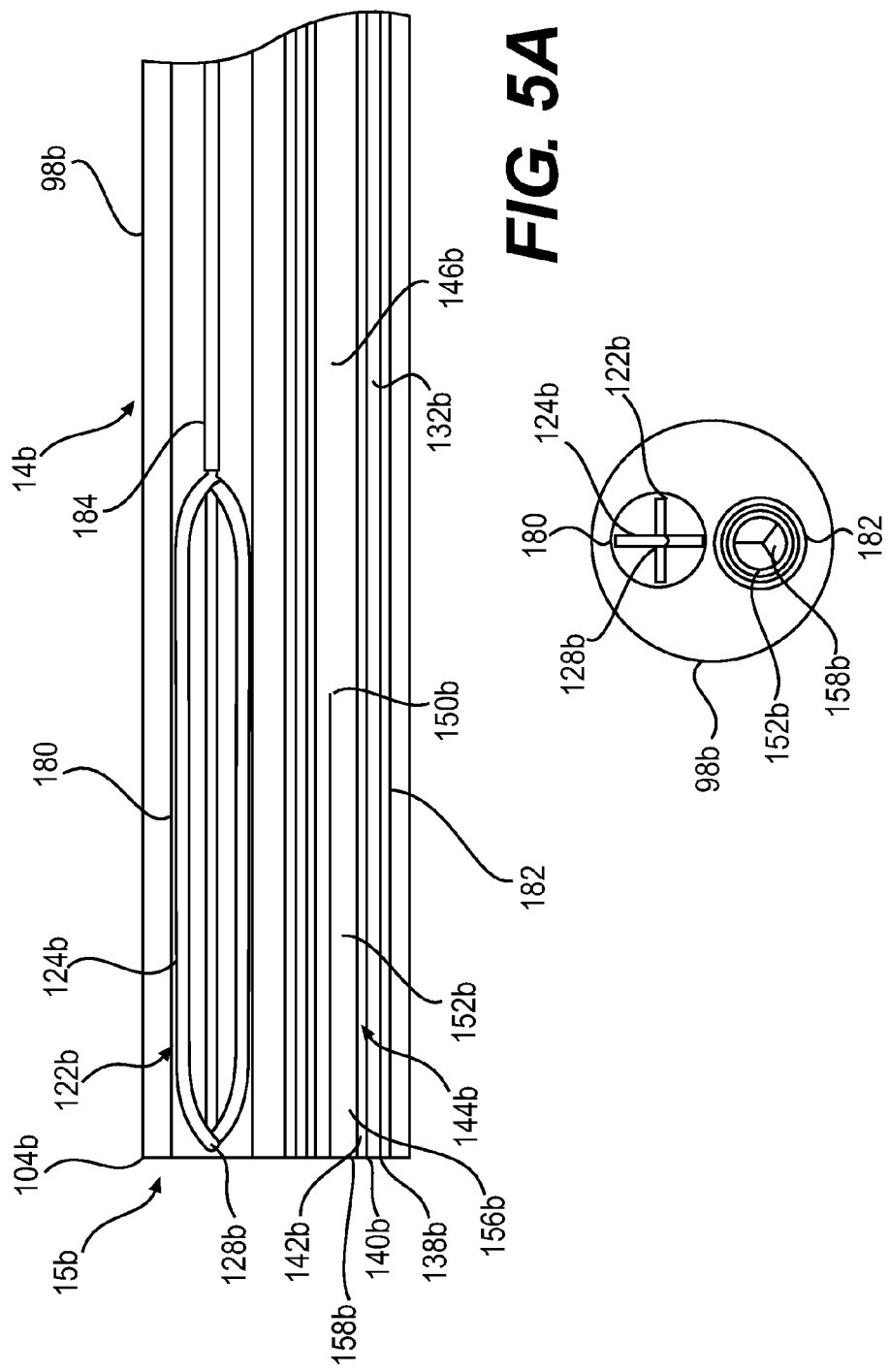
FIG. 5A is a cross-sectional side view of an embodiment of a distal portion of the device of FIG. 4, according to aspects of the present disclosure.
FIG. 5B is an end view of the embodiment of the distal portion of the device of FIG. 5A, according to aspects of the present disclosure.
Figure 6:
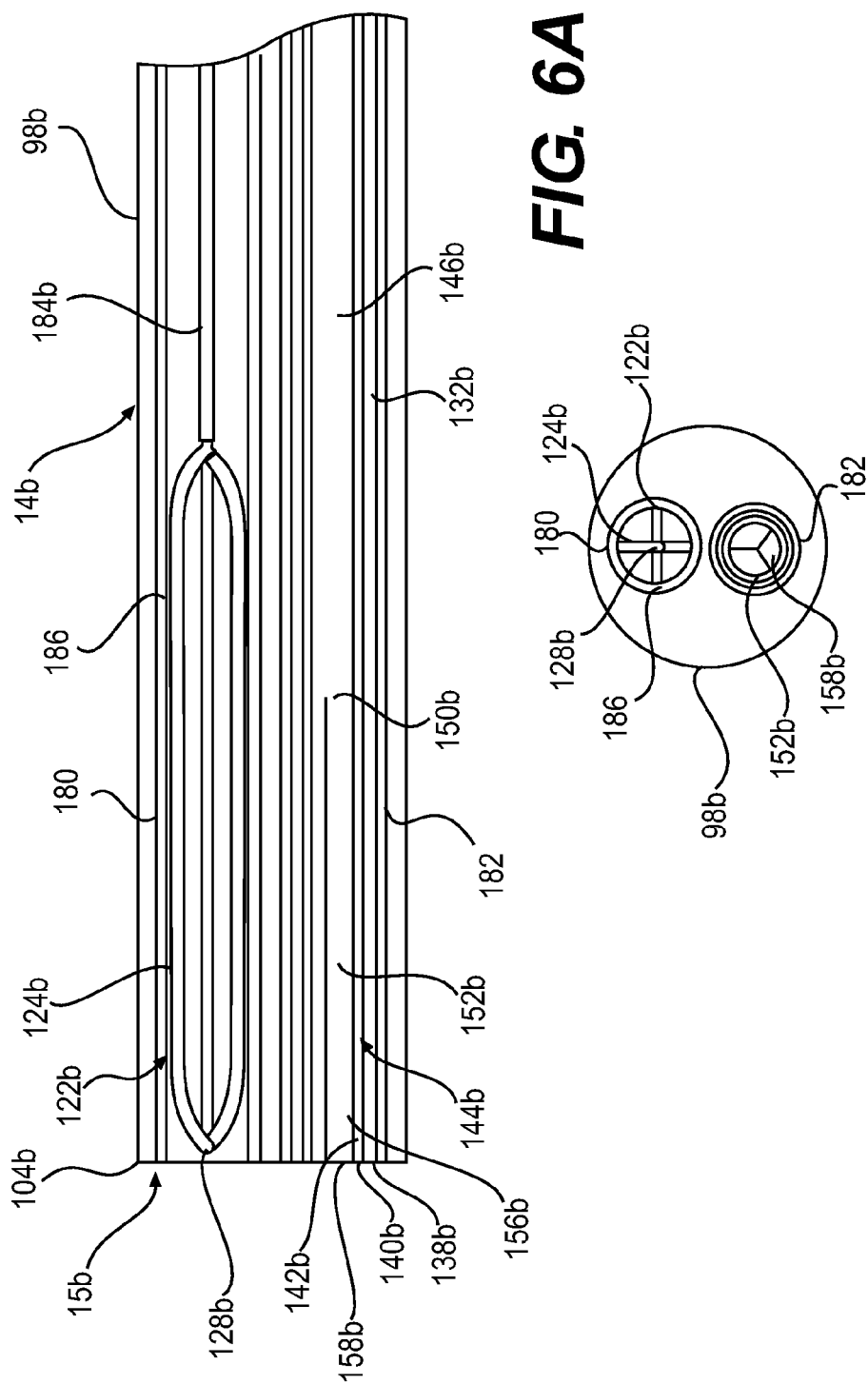
FIG. 6A is a cross-sectional side view of another embodiment of the distal portion of the device of FIG. 4, according to aspects of the present disclosure.
FIG. 6B is an end view of the embodiment of the distal portion of the device of FIG. 6A, according to aspects of the present disclosure.

FIG. 4 shows a cross-sectional side view of an alternative exemplary embodiment of the device 10, according to aspects of the present disclosure. In this embodiment, the horizontal passage 66 of the first button 56 may receive a basket stem 184, a forceps sheath 132b, and a forceps 144b of an instrument assembly 15b (FIGS. 5A and 6A). A longitudinal axis of the basket stem 184 may extend alongside the longitudinal axes of the forceps sheath 132b and forceps 144b. The forceps sheath 132b and forceps 144b may lie outside of the basket stem 184. The longitudinal axis of the basket stem 184 may be parallel to the longitudinal axes of the forceps sheath 132b and forceps 144b. The horizontal passage 80 of the second button 70 may receive the forceps sheath 132b and forceps 144b of the instrument assembly 15b. The horizontal passage 94 of the third button 88 may receive the forceps 144b of the instrument assembly 15b.

A sheath assembly 14b may include an outer sheath 98b. The outer sheath 98b may include a proximal end, having a proximal opening 102(b), coupled to the distal coupling element 20. A distal end 104b of the outer sheath 98b may have two distal openings corresponding to two lumens 180 and 182 running lengthwise through the outer sheath 98b. The lumens 180 and 182 may be in communication with the central passage 24 (FIG. 1A) of the main body 22 via the coupling element 20. The lumens 180 and 182 may be substantially parallel, although non-parallel orientations are also contemplated. The lumens 180 and 182 may have the same diameter, but different diameters are also contemplated and may be selected based on the diameter of the instrument to be inserted through the particular lumen. In some embodiments, the interior surfaces of the outer sheath 98 or 98b may be coated with a lubricious material, such as a polytetrafluoroethylene (PTFE) like TEFLON, polyvinylchloride, high-density polyethylene (HDPE), or the like, that may reduce friction between the interior surfaces and the outer surfaces of instruments that may come into contact with the interior surfaces. It is also contemplated that the interior surfaces of the outer sheath 98 or 98b may be coated with a plurality of coatings including one or more layers of a PTFE like TEFLON, polyvinylchloride, HDPE, and/or any other suitable or similar materials. The plurality of coatings may be arranged concentrically or non-concentrically around interior surfaces of the outer sheath 98 or 98b. It is also contemplated that in some embodiments the exterior surfaces of the outer sheath 98 or 98b may include a polyether block amide like PEBAX, polyethylene, polyurethane, polyolefin, or any other suitable polymeric or biocompatible material.

The lumen 180 of the outer sheath 98b may receive the basket stem 184 of the instrument assembly 15b. The basket stem 184 may have a proximal end 112b coupled to the first button unit 54. For example, the basket stem 184 may be coupled to the first button 56 by being clamped or otherwise mechanically secured between surfaces of the first button 56 and the holding member 64. Alternatively, the proximal end 112b of the basket stem 184 may be joined to the first button unit 56 using any suitable attachment mechanism such as an adhesive or by melting/melted attachment. The basket stem 184 may be reciprocally slidable within the handle housing 16 and the lumen 180 of the outer sheath 98b. For example, when the first button unit 54 is moved proximally, the basket stem 184 may slide proximally within and relative to the handle housing 16 and the outer sheath 98b. When the first button 56 is moved distally, the basket stem 184 may slide distally within and relative to the handle housing 16 and outer sheath 98b.

The distal portion of the basket stem 184 may be coupled to a basket 122b (FIGS. 5A, 5B, 6A, and 6B). The basket 122b may move between a contracted state (FIG. 5A), where the basket 122b is restrained by walls forming the lumen 180 of the outer sheath 98b, and an expanded state (FIG. 7), where the basket 122b is extended out of the outer sheath 98b. The basket 122b may include legs or struts 124b. The struts 124b may be inherently biased to move toward the expanded state in the absence of a restraining force keeping them in the contracted state. Any suitable number of struts may be used. A distal end of the basket 122b may include a tip 128b. The tip 128b include distal ends of the struts 124b. For example, the tip 128b may include one or more knots formed by distal ends of the struts 124b, for coupling the distal ends of the struts 124b. Additionally or alternatively, it is contemplated that the struts 124b may be bent, welded, pinned, rolled, or joined by any other suitable mechanical coupling at the tip 128b.

The lumen 182 in the outer sheath 98b may slidably receive the forceps sheath 132b of the instrument assembly 15b. The longitudinal axis of the lumen 182 may be parallel to the longitudinal axis of the lumen 180. Alternatively, the longitudinal axes of the lumens 180 and 182 may be angled relative to each other. The forceps sheath 132b may have a proximal end 134b (FIG. 4), coupled to the second button unit 68. For example, the forceps sheath 132b may be coupled to the second button unit 68 by being clamped between surfaces of the holding member 78 and the second button 70. Alternatively, the proximal end 134b of the forceps sheath 132b may be joined to the second button 70 using any suitable attachment mechanism such as an adhesive or by melting/melted attachment. The proximal end 134b may have a proximal opening 136b in communication with the horizontal passage 80 within the second button 70. The forceps sheath 132b may be reciprocally slidable within and relative to the handle housing 16. For example, when the second button 70 is moved proximally, the forceps sheath 132b may slide proximally within and relative to the handle housing 16. When the second button 70 is moved distally, the forceps sheath 132b may slide distally within and relative to the handle housing 16. The forceps sheath 132b may have a distal end 138b and a distal opening 140b (FIGS. 5A, 5B, 6A, and 6B). A portion of the distal end 138b may extend out from the distal end of the outer sheath 98b when the forceps sheath 132b is moved distally.

The forceps sheath 132b may slidably receive the forceps 144b in its lumen 142b. Longitudinal axes of the forceps sheath 132b and forceps 144b may be coaxial. Longitudinal axes of the basket stem 184 and basket 122b may be coaxial. The longitudinal axes of the forceps sheath 132b and forceps 144b may be parallel to the longitudinal axes of the basket stem 184 and basket 122b. The forceps 144b may form part of the instrument assembly 15b. The forceps 144b may include a proximal shaft 146b. The shaft 146b may have a proximal end 148b (FIG. 4), coupled to the third button unit 86. For example, the proximal shaft 146b may be coupled to the third button 88 by clamping of the proximal shaft 146b by surfaces of the screw 96 and the third button 88. Alternatively, the proximal shaft 146b may be joined to the third button 88 using any suitable adhesive. Distal arms 152b (FIGS. 5A, 5B, 6A, 6B, and 7) may be provided at a distal end 150b of the proximal shaft 146b. Each of the arms 152b may include a proximal end 154b, distal end 156b, and distal tip 158b.

The forceps 144b may be slidable reciprocally (e.g., proximally and distally) relative to and within the handle housing 16 and the forceps sheath 132b. For example, when the third button unit 86 is moved proximally, the forceps 144*b* may slide proximally relative to and within the handle housing 16 and the forceps sheath 132*b*. When the third button 88 is moved distally, the forceps 144*b* may slide distally relative to and within the handle housing 16 and the forceps sheath 132*b*. At least a portion of the arms 152*b* may extend out from the distal end 138*b* of the forceps sheath 132*b* when the forceps 144*b* is moved distally relative to the forceps sheath 132*b*. It is also contemplated that the forceps 144*b* and forceps sheath 132*b* may move together when engagement between the screw 96 of the third button unit 86 and ends of the slot 84 of the second button unit 68 links movement of the second and third button units 68 and 86. For example, the forceps 144*b* and forceps sheath 132*b* may move together with the forceps 144*b* enclosed within the forceps sheath 132*b*, and/or with the forceps 144*b* extending out from the forceps sheath 132*b*.

Figure 7:
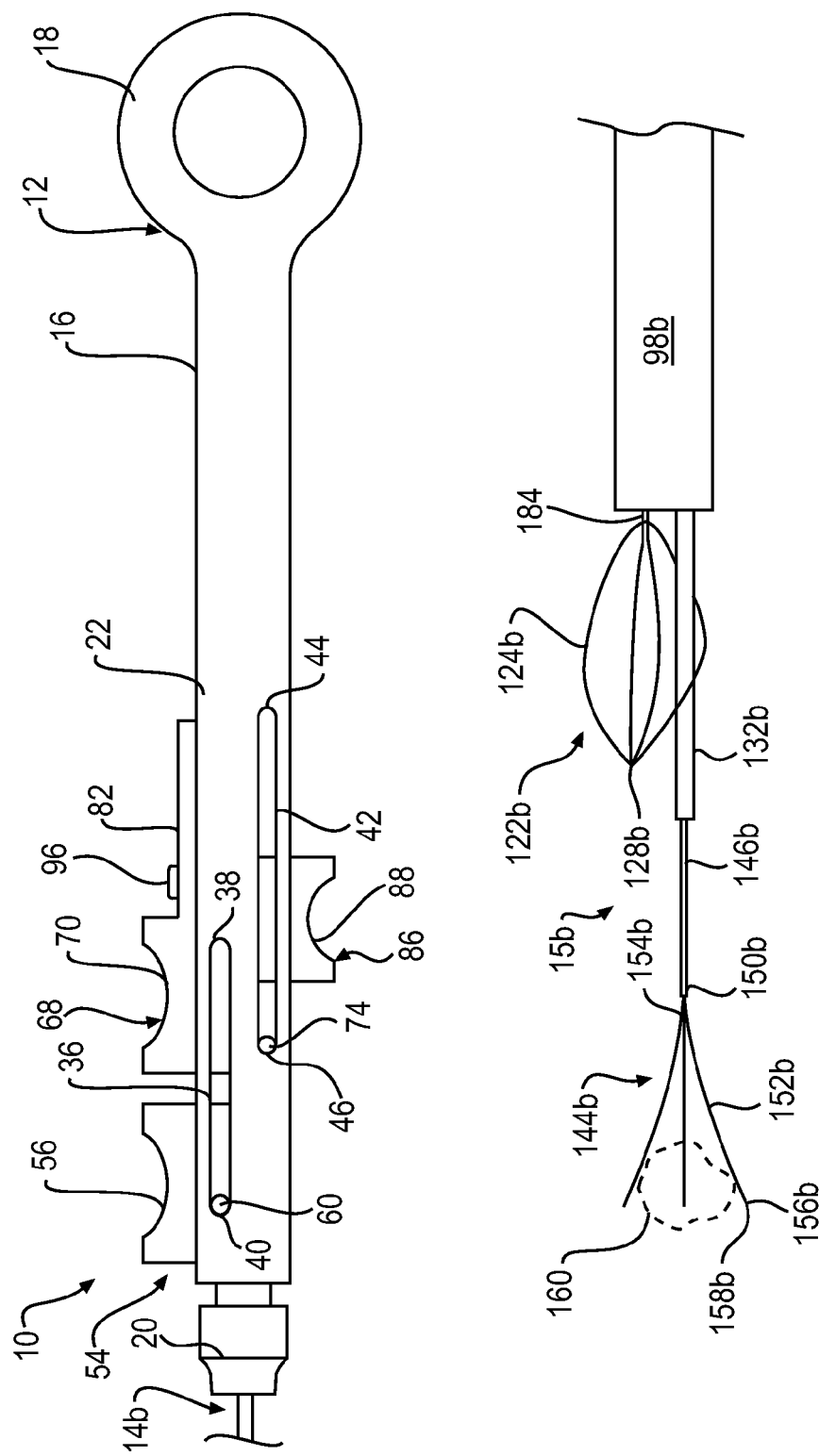
FIG. 7 illustrates the device of FIG. 4 in an exemplary state of operation, according to aspects of the present disclosure.

The distal arms 152*b* may have a contracted state (FIGS. 5A, 5B, 6A, and 6B), and an expanded state (FIG. 7). The distal arms 152*b* may be inherently biased to expand radially outwardly to the expanded state in the absence of a restraining force. The forceps sheath 132*b* may provide the restraining force to keep the distal arms 152*b* in the contracted state when the distal arms 152*b* are within the lumen 142*b*. When the distal arms 152*b* protrude from the distal end 138*b* of the forceps sheath 132*b*, they may expand radially outwardly.

As shown in FIG. 5A, at least a portion of the forceps 144*b* may extend along/beside the basket stem 184. The longitudinal axis of the basket stem 184 may extend alongside the longitudinal axes of the forceps sheath 132*b* and forceps 144*b*. For example, the longitudinal axis of the basket stem 184 may be parallel to the longitudinal axes of the forceps sheath 132*b* and forceps 144*b*. The basket 122*b* and the forceps 144*b* may be made of a super elastic, elastic, or shape memory alloy such as nitinol or any other suitable material. A person of ordinary skill in the art will understand that in addition to the basket 122*b* and the forceps 144*b*, the device 10 may additionally include other end-effectors such as, but not limited to, morcellators, needles, hooks, forceps, energy delivery mechanisms, guide wires, scissors, and balloons. It is also contemplated that the struts 124*b* and/or the arms 152*b* may be electrodes configured to conduct electrical energy, such as radiofrequency energy. In such an embodiment, the basket stem 184, forceps sheath 132*b*, and/or forceps 144*b* may include one or more electrical conductors coupled to an electrical energy source in or coupled to the handle assembly 12.

FIGS. 6A and 6B show another embodiment of the exemplary device 10. This embodiment includes a basket sheath 186 extending through the lumen 180. The basket 122*b* and basket stem 184 may be slidable within a central lumen of the basket sheath 186. The basket sheath 186 may help constrain the basket 122*b* in its collapsed configuration. It is also contemplated that the basket sheath 186 may be made of a lubricious material, such as a polytetrafluoroethylene (PTFE) like TEFLON, polyvinylchloride, high-density polyethylene (HDPE), or the like, that may reduce friction between the basket sheath 186 and the basket stem 184 and/or basket 122*b*. Additionally or alternatively, an interior surface of the basket sheath 186 may be coated with lubricious material, such as a polytetrafluoroethylene (PTFE) like TEFLON, polyvinylchloride, high-density polyethylene (HDPE), or the like.

It is contemplated that one or more sheaths (e.g., outer sheath 98, outer sheath 98*b*, basket sheath 110, basket sheath 186, forceps sheath 132, and forceps sheath 132*b*) may include reinforcement. The reinforcement may include, for example, one or more reinforcing members, including one or more of wires, coils, and/or braids on an interior or exterior surface of the sheath, or within material forming a wall of the sheath. The reinforcing members may be made of metal/metal alloys including Nitinol, stainless steel, and/or any other suitable materials. It is contemplated that the reinforcing members may be annealed to the desired hardness or softness.

It is contemplated that one or more sheaths (e.g., outer sheath 98, outer sheath 98*b*, basket sheath 110, basket sheath 186, forceps sheath 132, and forceps sheath 132*b*) may have varying flexibility along its longitudinal length. For example, the sheath may be formed with a portion having greater flexibility by changing the durometer and/or thickness of plastic components of the sheath, so the durometer and/or thickness is different than the durometer and/or thickness at another portion. Additionally or alternatively, characteristics of the reinforcing members may be altered as one moves from proximal to distal ends, to vary the flexibility of the one or more sheaths.

It is contemplated that one or more sheaths (e.g., outer sheath 98, outer sheath 98*b*, basket sheath 110, basket sheath 186, forceps sheath 132, and forceps sheath 132*b*) may be shortened by a distance, and that a push/pull wire may be provided on a proximal end of the sheath. The push/pull wire may have a length similar to the distance. For example, one or more of the basket sheath 110, basket sheath 186, forceps sheath 132, and forceps sheath 132*b* may be shortened, with a proximal end of the sheath being coupled to its corresponding button (e.g., first button 56 or second button 70) by a push/pull wire.

It is contemplated that outer sheath 98 and/or outer sheath 98*b* may include one or more additional lumens. The additional lumen may receive one or more tools including, for example, a laser, ultrasound, or pneumatic lithotripsy tool. The tool may be used in combination with one or more of basket 122, basket 122*a*, basket 122*b*, forceps 144, and forceps 144*b* to manipulate and/or process objects/stones.

It is contemplated that one or more of the buttons (e.g., first button 56, second button 70, and third button 88) of the button units (e.g., first button unit 54, second button unit 68, and third button unit 86) may be a locking button. The locking button may remain in one position relative to the main body 22, until released to move to another position. The locking button may include a releasable locking mechanism that may be biased to lock the button in position. A user may provide a force on the releasable locking mechanism (e.g., by pressing down on the releasable locking mechanism) to overcome the bias and release the locking button, allowing the user to move the locking button proximally/distally to a desired position. At the desired position, the user may cease providing the force, allowing the locking button to lock and remain at the desired position. The releasable locking mechanism allows the locking button, and components moved/actuated by the locking button, to remain fixed in position until movement/actuation is desired by the user.

It is contemplated that one or more of the buttons (e.g., first button 56, second button 70, and third button 88) of the button units (e.g., first button unit 54, second button unit 68, and third button unit 86) may be locked to another of the one or more buttons. Locking one button to another button may cause the buttons to move in unison, until the buttons are released to move individually. For example, one button may include a first member of a releasable locking mechanism configured to releasably lock/unlock with a second member of the releasable locking mechanism on another button. The releasable locking mechanism may be biased to keep the first and second members in engagement. A user may provide a force on the releasable locking mechanism (e.g., by pressing on the releasable locking mechanism) to overcome the bias and release the first member from the second member, allowing one button to move relative to the other button.

It is contemplated that one or more of basket 122, basket 122a, basket 122b, forceps 144, and forceps 144b may include one or more wires. For example, struts 124, 124a, and 124b may be formed by wires. Additionally or alternatively, arms 152 and 152b may be formed by wires. The wires may have any suitable thickness and cross-sectional profile (e.g., circular, elliptical, rectangular, polygonal, and irregular), or other characteristic.

It is contemplated that in some embodiments, one or more of basket 122, basket 122a, basket 122b, forceps 144, and forceps 144b may move to the expanded state by moving one or more of outer sheath 98, outer sheath 98b, basket sheath 110, basket sheath 186, forceps sheath 132, and forceps sheath 132b proximally relative to the basket and/or forceps. In such an embodiment, the basket and/or forceps may be moved to the contracted state by moving one or more of the sheaths distally relative to the basket and/or forceps. It is also contemplated that in some embodiments, the basket and/or forceps and the one or more sheaths may be moved to achieve expansion and contraction.

FIGS. 3A to 3F and 7 show embodiments of the device 10 in exemplary states of operation, according to aspects of the present disclosure. As shown in FIG. 3A, the button units 54, 68, and 86 may be moved proximally to their proximalmost positions. The proximalmost position of the first button unit 54 may correspond to the position where the pin 60 engages the proximal end 38 of the slot 36. Referring to the embodiment of the device 10 corresponding to FIG. 2A, when the first button unit 54 is in its proximalmost position, the basket sheath 110 may also be in its proximalmost position, where the basket 122 is retracted into the outer sheath 98, and is held in its contracted state by the outer sheath 98. Referring to the embodiment of the device 10 corresponding to FIG. 2C, when the first button unit 54 is in its proximalmost position, the basket sheath 110 may also be in its proximalmost position, where the basket 122a is retracted into the outer sheath 98, and is held in its contracted state by the outer sheath 98. Referring to the embodiment of the device 10 corresponding to FIG. 5A, when the first button unit 54 is in its proximalmost position, the basket stem 184 may also be in its proximalmost position, where the basket 122b is retracted into the lumen 180 of the outer sheath 98, and is held in its contracted state by the outer sheath 98. Referring to the embodiment of the device 10 corresponding to FIG. 6A, when the first button unit 54 is in its proximalmost position, the basket stem 184 may also be in its proximalmost position, where the basket 122b is retracted into the basket sheath 186, and is held in its contracted state by the basket sheath 186.

The proximalmost position of the second button unit 68 may correspond to the position where the pin 74 engages the proximal end 44 of the slot 42. When the second button unit 68 is in its proximalmost position, the forceps sheath (e.g., one of the forceps sheaths 132 and 132b) also may be in its proximalmost position, where the forceps sheath is retracted within the outer sheath (e.g., one of the outer sheaths 98 and 98b).

The proximalmost position of the third button unit 86 may correspond to the position where the screw 96 engages the proximal end of the slot 84 of the second button unit 68. When the third button unit 86 is in its proximalmost position, the forceps (e.g., one of the forceps 144 and 144b) may also be in its proximalmost position, with the arms (e.g., one of the arms 152 and 152b) retracted into its forceps sheath (e.g., one of the forceps sheaths 132 and 132b) and held in their contracted states by the forceps sheath.

With the handle assembly 12 configured as shown in FIG. 3A, the distal end of one embodiment of the device 10 may be in the state shown in FIG. 2A, the distal end of another embodiment of the device 10 may be in the state shown in FIG. 2C, the distal end of another embodiment of the device 10 may be in the state shown in FIG. 5A, or the distal end of another embodiment of the device 10 may be in the state shown in FIG. 6A. These states may be helpful for inserting the device 10 into a subject's body, and navigating the device 10 to a target area, since the basket (e.g., one of the baskets 122, 122a, and 122b), and the arms (e.g., one of the arms 152 and 152b) of the forceps (e.g., one of the forceps 144 and 144b) are contracted or collapsed.

The device 10 may be inserted into the subject's body and navigated therein to position the distal end of the sheath 14 or the sheath 14b at or near a target area, where an object targeted for removal is located. The handle housing 16 may remain outside of the subject's body, where it is capable of being grasped and manipulated by the user. It is contemplated, for example, that the sheath 14 or the sheath 14b may be inserted directly into a subject's body through a body lumen, or may be inserted through a channel in an introducer (not shown). The introducer may include, for example, an endoscope, cystoscope, catheter, or other suitable introduction sheath. The user may move the device 10 in insertion and withdrawal directions by pushing and pulling on the gripping member 18. The user may use a detection mechanism, such as fluoroscopy or other imaging device, to determine the location of the sheath 14 or the sheath 14b in the subject's body. As such, the sheath 14, sheath 14b, instrument assembly 15, instrument assembly 15a, and/or instrument assembly 15b may include one or more portions that are radiopaque, or that have one or more radiopaque markings.

As shown in FIG. 3B, using the state of the device in FIG. 3A as an exemplary starting point, a user may slide the first button unit 54 distally, while the second and third button units 68 and 86 remain static. Referring to the embodiment of the device 10 corresponding to FIG. 2A, when the first button unit 54 is advanced distally, the basket sheath 110 coupled to the first button unit 54, may also advance distally relative to the handle housing 16, forceps sheath 132, and forceps 144. A distal portion of the basket sheath 110 may extend out of the distal end 104 of the outer sheath 98. The endcap 128 and struts 124 of the basket 122 may disengage from the still retracted forceps sheath 132, and a proximal portion of the basket sheath 110 may slide over the forceps sheath 132. The endcap 128 may exit first from the outer sheath 98, followed by the struts 124.

Referring to the embodiment of the device 10 corresponding to FIG. 2C, when the first button unit 54 is advanced distally, the basket sheath 110 coupled to the first button unit 54, may also advance distally relative to the handle housing 16, forceps sheath 132, and forceps 144. The basket 122a may extend out of the distal end 104 of the outer sheath 98, and a proximal portion of the basket sheath 110 may slide over the forceps sheath 132. The tip 128a may exit first from the outer sheath 98, followed by the struts 124a. The extended basket 122a is shown in FIG. 3F.

Referring to the embodiment of the device 10 corresponding to FIGS. 5A and 6A, when the first button unit 54 is advanced distally, the basket stem 184 coupled to the first button unit 54, may also advance distally relative to the handle housing 16. The basket 122b may extend out of the distal end 104b of the outer sheath 98b. The tip 12b may exit first from the outer sheath 98b, followed by the struts 124b. The extended basket 122b is shown in FIG. 7.

As the struts (e.g., struts 124, 124a, or 124b) exit from the outer sheath (e.g., one of the sheaths 98 and 98b), they may move radially outwardly, and thus, the basket (e.g., one of the baskets 122, 122a, and 122b) may move toward its expanded state. The degree of expansion of the basket may be controlled by adjusting the lengths that its struts extend out from the outer sheath. The user may use the markings 41 to track extension of the struts. The first button unit 54 may be moved to its distalmost position, wherein the pin 60 engages the distal end of the slot 36, to fully extend and expand the basket.

The expanded basket (e.g., one of the baskets 122, 122a, and 122b) may be maneuvered against an object to capture the object within the basket. With the object captured, the first button unit 54 may be moved proximally to at least partially retract the basket, thus moving the basket towards its contracted state and closing their its struts (e.g., struts 124, 124a, or 124b) around the object. The retraction of the baskets 122 and 122a may also help trap the object between the baskets 122 and 122a and the distal end 104 of the sheath 98, and increase the holding force exerted on the object by the baskets 122 and 122a and the sheath 98. The retraction of the basket 122b may also help trap the object between the basket 122b and the distal end 104b of the sheath 98b, and increase the holding force exerted on the object by the basket 122b and the sheath 98b. The device 10 may be withdrawn from the subject's body along with the grasped object.

In some instances, the diameter of the basket (e.g., one of the baskets 122, 122a, and 122b) may be too large to pass through a constriction in the subject's body, due to the grasped object keeping the basket in its partially expanded state. Thus, the constriction may block withdrawal of the device 10 and the grasped object from the subject's body. The grasped object may have to be released from the device 10 in order to withdraw the device 10 out of the subject's body. The first button unit 54 may be moved distally to extend and expand the basket, exposing a longer length of the struts (e.g., struts 124, 124a, or 124b) from the outer sheath (e.g., one of the outer sheaths 98 and 98b), and allowing larger gaps to develop between the struts. The second button unit 68 may be moved distally, driving the forceps sheath (e.g., one of the forceps sheaths 132 and 132b) distally. The distal end of the forceps sheath may engage the object, and may push the object through the gaps between the struts, possibly deforming one or more of the struts during pushing. Continued pushing may force the object out of the interior of the basket. The third button unit 68 may be moved distally by the distal movement of the second button unit 68, due to engagement between the proximal end of the slot 84 of the second button unit 68 and the screw 96 of the third button unit 86. Thus, the forceps (e.g., one of the forceps 144 and 144b) may move distally with the forceps sheath during the pushing step. The forceps may provide the forceps sheath with added strength/rigidity, to help force the object out of the basket.

With the stone 160 released, the first button unit 54 may be moved proximally to contract the basket (e.g., one of the baskets 122, 122a, and 122b), and/or the second and third button units 68 and 86 may be moved proximally to retract the forceps (e.g., one of the forceps 144 and 144b) and forceps sheath (e.g., one of the forceps sheaths 132 and 132b), to help configure the device 10 for removal from the subject. Alternatively, it is contemplated that the device 10 may be removed with the basket, the forceps sheath, and/or forceps extended, if the components fit through the constriction after the object is released.

As shown in FIG. 3C, using the state of the handle assembly 12 in FIG. 3A as an exemplary starting point, the embodiment of the device 10 corresponding to FIG. 2A may be manipulated such that the forceps 144 may be used to grasp an object. This may be accomplished by sliding the third button unit 86 distally, while leaving the first and second button units 54 and 68 in their proximalmost positions. During this movement, the screw 96 of the third button unit 86 may slide distally within the slot 84 of the second button unit 68. Because the first and second button units 54 and 68 remain in their proximalmost positions, the forceps 144 may move distally relative to the outer sheath 98, basket sheath 110, and the forceps sheath 132. The arms 152 of the forceps 144 may extend out of the sheaths 98, 110, and 132. Once extended out, the arms 152 may expand radially outward to engage and receive the targeted object. The user may move the third button unit 86 proximally to at least partially draw the arms 152 back into the forceps sheath 132, causing the arms 152 to move toward the contracted state, thus increasing their grip on the object. The device 10 and the grasped object may then be withdrawn from the subject's body.

Referring to the embodiment of the device 10 corresponding to FIG. 2C, and using the state of the handle assembly 12 shown in FIG. 3A as a starting point, the device 10 may be manipulated such that the forceps 144 may be used to grasp an object. This may be accomplished by sliding the third button unit 86 distally, while leaving the first and second button units 54 and 68 in their proximalmost positions. Because the first and second button units 54 and 68 remain in their proximal most positions, the forceps 144 may move distally relative to the outer sheath 98, basket sheath 110, basket 122a, and forceps sheath 132. The forceps 144 may move between adjacent struts 124a of the basket 122a and along a side of the tip 128a. The arms 152 of the forceps 144 may extend out of the sheaths 98 and 132. Once extended out, the arms 152 may expand radially outward to engage and receive the targeted object. The expanded state of the arms 152 is shown in FIG. 3F. The user may move the third button unit 86 proximally to at least partially draw the arms 152 back into the forceps sheath 132, causing the arms 152 to move toward the contracted state, thus increasing their grip on the object. The device 10 and the grasped object may then be withdrawn from the subject's body.

Referring to the embodiments of the device 10 corresponding to FIGS. 5A and 6A, and using the state of the handle assembly 12 shown in FIG. 3A as a starting point, the device 10 may be manipulated such that the forceps 144b may be used to grasp an object. This may be accomplished by sliding the third button unit 86 distally, while leaving the first and second button units 54 and 68 in their proximalmost positions. Because the first and second button units 54 and 68 remain in their proximal most positions, the forceps 144b may move distally relative to the outer sheath 98b and forceps sheath 132b. The arms 152b of the forceps 144b may extend out of the sheaths 98b and 132b. Once extended out, the arms 152b may expand radially outward to engage and receive the targeted object. The expanded state of the arms 152b is shown in FIG. 7. The user may move the third button unit 86 proximally to at least partially draw the arms 152b back into the forceps sheath 132b, causing the arms 152b to move toward the contracted state, thus increasing their grip on the object. The device 10 and the grasped object may then be withdrawn from the subject's body.

As shown in FIG. 3D, using the state of the handle assembly 12 in FIG. 3A as an exemplary starting point, the reach of the forceps 144 may be extended distally beyond that which is shown in FIG. 3C, to grasp an object. The steps may include moving the second button unit 68 distally. The proximal end of the slot 84 of the second button unit 68 may engage the screw 96 of the third button unit 86 during distal movement of the second button unit 68, resulting in the third button unit 86 being forced in the distal direction. Thus, referring to the embodiment of the device corresponding to FIG. 2A, the forceps sheath 132 and the forceps 144 may move as a unit relative to the outer sheath 98 and the basket sheath 110, and may extend distally out of the sheaths 98 and 110. The forceps 144 may remain contracted within the forceps sheath 132. During the extension, the forceps 144 and forceps sheath 132 may pass through the basket 122 and the end cap 128.

Alternatively, referring to the embodiment of the device 10 corresponding to FIG. 2C, the forceps sheath 132 and the forceps 144 may move as a unit relative to the outer sheath 98, basket sheath 110, and basket 122*a*, and may extend distally out of the sheath 98. During the extension, the forceps sheath 132 and forceps 144 may extend between struts 124*a* and beside the tip 128*a*. The extended forceps sheath 132 is shown in FIG. 3F. The forceps 144 may remain contracted within the forceps sheath 132.

Alternatively, referring to the embodiment of the device 10 corresponding to FIGS. 5A and 6A, the forceps sheath 132*b* and the forceps 144*b* may move as a unit relative to the outer sheath 98*b*, and may extend distally out of the lumen 182 of the sheath 98*b*. The extended forceps sheath 132*b* and the forceps 144*b* is shown in FIG. 7. The forceps 144*b* may remain contracted within the forceps sheath 132*b*.

The third button unit 86 then may be moved distally relative to the second button unit 68, with the screw 96 moving distally from the proximal end of the slot 84 of the second button unit 68 toward the distal end of the slot 84. As the third button unit 86 moves distally relative to the second button unit 68, the forceps (e.g., one of the forceps 144 and 144*b*) may move distally relative to the forceps sheath (e.g., one of the forceps sheaths 132 and 132*b*). The arms (e.g., arms 152 or 152*b*) may be extended out from the forceps sheath. Once extended out, the arms may expand radially outward to engage and grasp the targeted object. The extended arms are shown in FIGS. 3D through 3F and 7.

If the screw 96 of the third button unit 86 comes into contact with the distal end of the slot 84, moving the second button unit 68 proximally may cause the third button unit 86 to move proximally, due to engagement between the screw 96 and the distal end of the slot 84. This may draw the forceps sheath (e.g., one of the forceps sheaths 132 and 132*b*), forceps (e.g., one of the forceps 144 and 144*b*), and grasped object toward the outer sheath (e.g., one of the outer sheaths 98 and 98*b*). Sliding the third button unit 86 proximally relative to the second button unit 68, and causing the screw 96 to move toward the proximal end of the slot 84, may at least partially draw the arms (e.g., arms 152 or 152*b*) back into their forceps sheath, increasing their grip on the object. The device 10 and the grasped object may be withdrawn from the subject's body.

As shown in FIGS. 3E and 3F, the embodiments of the device 10 corresponding to FIGS. 2A and 2C, respectively, may be manipulated to remove an object, such as a stone 160, using the basket (e.g., one of the baskets 122 and 122*a*) and the arms 152 of the forceps 144. The steps may include extending and expanding the basket in the manner shown in FIGS. 3E and 3F by moving the first button unit 54 distally. Referring to the embodiment of the device 10 corresponding to FIG. 2A, extension of the basket 122 may free the endcap 128 from the forceps sheath 132 and the forceps 144. Alternatively, referring to the embodiment of the device 10 corresponding to FIG. 2C, extension of the basket 122*a* may separate the basket 122*a* from the forceps sheath 132 and the forceps 144. With the basket extended and expanded, the next step may include extending the forceps sheath 132 and forceps 144 by moving the second and third button units 68 and 86 distally. By moving the forceps sheath 132 distally beyond the basket with the forceps 144 in an at least partially contracted state, and then extending the forceps 144 from the forceps sheath 132, the probability of the forceps 144 becoming tangled with the struts 124 and/or the endcap 128 of the basket 122, or the struts 124*a* and/or tip 128*a* of the basket 122*a*, may be reduced. The arms 152 of the forceps 144 may engage and receive/grasp the stone 160. During this step, the longitudinal axes of portions of the forceps sheath 132 and forceps 144 may be parallel to or angled relative to the longitudinal axis of the basket sheath 110.

The second and third button units 68 and 86 may be moved proximally to force the stone 160 between the struts (e.g., struts 124 or 124*a*) and into the interior of the basket (e.g., one of the baskets 122 and 122*a*). For example, the third button unit 86 may be moved proximally to try to retract at least a portion of the arms 152 into the forceps sheath 132, thus increasing the grip of the arms 152 on the stone 160. The presence of the stone 160 may inhibit full retraction of the arms 152, due to the diameter of the stone 160 and/or the expanded arms 152. Further proximal movement of the third button unit 86 and the forceps 144 will force the forceps sheath 132, and the second button unit 68, proximally together with the third button unit 86.

The first button unit 54 may be moved proximally to contract the basket (e.g., one of the baskets 122 and 122*a*) around the stone 160 and the arms 152, while drawing the stone 160 closer to the distal end 104 of the outer sheath 98. The stone 160, which may be engaged by the basket, and the arms 152, may be held more securely than if held by only one of the arms 152 and the basket. The device 10 and the stone 160 then may be removed from the subject's body.

In some instances, the diameter of the basket (e.g., one of the baskets 122 and 122*a*), arms 152, and/or the stone 160 may be too large to fit a constriction in the subject's body, due for example to the stone 160 keeping the basket and/or the arms 152 in partially expanded states. Thus, the constriction may block withdrawal of the device 10 and the stone 160 from the subject's body. The stone 160 may have to be released from the device 10 in order to withdraw the device 10. To do this, the first button unit 54 may be moved distally to expand the basket, creating larger gaps between the struts (e.g., struts 124 or 124*a*). The second button unit 68 may be moved distally to move the forceps sheath 132 distally. The distal end 138 of the forceps sheath 132 may engage the expanded arms 152, and possibly a portion of the stone 160, and may push the arms 152 and/or the stone 160 through the gaps between the struts and out of the interior of the basket. The third button unit 68 may be forced distally by the distal movement of the second button unit 68 due to engagement of the forceps sheath 132 with the expanded arms 152 and/or stone 160, or by engagement between the proximal end of the slot 84 and the screw 96. The third button unit 86 then may be moved distally to extend the arms 152 out of the forceps sheath 132, allowing the arms 152 to expand outwardly to release the stone 160 from the arms 152.

With the stone 160 released, the first, second, and/or third button units 54, 68, and 86 may be moved proximally, to retract and contract the basket (e.g., one of the baskets 122 and 122a) and/or the arms 152, to assist with removing the device 10 from the subject's body. For example, the third button unit 86 may be moved proximally to retract the arms 152 back into the forceps sheath 132. When the arms 152 are retracted, the screw 96 may engage the proximal end of the slot 84, and thus, further proximal movement of the third button unit 86 may draw the second button unit 68 proximally, bringing the forceps sheath 132 and forceps 144 proximally into the basket and/or the basket sheath 110. This movement may continue until the pin 74 of the second button unit 68 reaches the proximal end 44 of the slot 42. The first button unit 54 may be moved proximally to retract the basket into the outer sheath 98. By retracting the forceps sheath 132 and forceps 144 before retracting the basket, contraction of the basket may not be obstructed by the forceps sheath 132 or forceps 144. However, it should be understood than retraction may be performed in any order. It is also contemplated that the device 10 may be removed with the basket, forceps sheath 132, and/or forceps 144 extended, if the components may fit through the constriction after the stone 160 is released.

As shown in FIG. 7, the embodiments of the device 10 corresponding to FIGS. 5A and 6A, respectively, may be manipulated to remove an object, such as a stone 160, using both the basket 122b and the arms 152b of the forceps 144b. The steps may include extending and expanding the basket 122b in the manner shown in FIG. 7 by moving the first button unit 54 distally.

With the basket 122b extended and expanded, the next step may include extending the forceps sheath 132b and forceps 144b by moving the second and third button units 68 and 86 distally. By moving the forceps sheath 132b distally beyond the basket 122b with the forceps 144b in an at least partially contracted state, and then extending the forceps 144b from the forceps sheath 132b, the probability of the forceps 144b becoming tangled with the struts 124b and/or the tip 128b of the basket 122b, may be reduced. The arms 152b of the forceps 144b may engage and receive/grasp the stone 160. During this step, the longitudinal axes of portions of the forceps sheath 132b and forceps 144b may be alongside (e.g., parallel to) and/or angled relative to the longitudinal axis of the basket stem 184.

The second and third button units 68 and 86 may be moved proximally to force the stone 160 between the struts 124b and into the interior of the basket 122b. For example, the third button unit 86 may be moved proximally to try to retract at least a portion of the arms 152b into the forceps sheath 132b, thus increasing the grip of the arms 152b on the stone 160. The presence of the stone 160 may inhibit full retraction of the arms 152b, due to the diameter of the stone 160 and/or the expanded arms 152b. Further proximal movement of the third button unit 86 and the forceps 144b will force the forceps sheath 132b, and the second button unit 68, proximally together with the third button unit 86.

The first button unit 54 may be moved proximally to contract the basket 122b around the stone 160 and the arms 152b, while drawing the stone 160 closer to the distal end 104b of the outer sheath 98b. The stone 160, which may be engaged by both the basket 122b and the arms 152b, may be held more securely than if held by only one of the arms 152b and the basket 122b. The device 10 and the stone 160 then may be removed from the subject's body.

In some instances, the diameter of the basket 122b, arms 152b, and/or the stone 160 may be too large to fit a constriction in the subject's body, due for example to the stone 160 keeping the basket 122b and/or the arms 152b in partially expanded states. Thus, the constriction may block withdrawal of the device 10 and the stone 160 from the subject's body. The stone 160 may have to be released from the device 10 in order to withdraw the device 10. To do this, the first button unit 54 may be moved distally to expand the basket 122b, creating larger gaps between the struts 124b. The second button unit 68 may be moved distally to move the forceps sheath 132b distally. The distal end 138b of the forceps sheath 132b may engage the expanded arms 152b, and possibly a portion of the stone 160, and may push the arms 152b and/or the stone 160 through the gaps between the struts 124b and out of the interior of the basket 122b. The third button unit 68 may be forced distally by the distal movement of the second button unit 68 due to engagement of the forceps sheath 132b with the expanded arms 152b and/or stone 160, or by engagement between the proximal end of the slot 84 and the screw 96. The third button unit 86 then may be moved distally to extend the arms 152b out of the forceps sheath 132b, allowing the arms 152b to expand outwardly to release the stone 160 from the arms 152b.

With the stone 160 released, the first, second, and/or third button units 54, 68, and 86 may be moved proximally, to retract and contract the basket 122b and/or the arms 152b, to assist with removing the device 10 from the subject's body. For example, the third button unit 86 may be moved proximally to retract the arms 152b back into the forceps sheath 132b. When the arms 152b are retracted, the screw 96 may engage the proximal end of the slot 84, and thus, further proximal movement of the third button unit 86 may draw the second button unit 68 proximally, bringing the forceps sheath 132b and forceps 144b proximally into the lumen 182. This movement may continue until the pin 74 of the second button unit 68 reaches the proximal end 44 of the slot 42. The first button unit 54 may be moved proximally to retract the basket 122b into the outer sheath 98b. By retracting the forceps sheath 132b and forceps 144b before retracting the basket 122b, contraction of the basket 122b may not be obstructed by the forceps sheath 132b or forceps 144b. However, it should be understood than retraction may be performed in any order. It is also contemplated that the device 10 may be removed with the basket 122b, forceps sheath 132b, and/or forceps 144b extended, if the components can fit through the constriction after the stone 160 is released.

The principles disclosed above can be applied to other types of devices and can be implemented in different ways without departing from the scope of the invention as defined by the claims. In particular, constructional details, including manufacturing techniques and materials, are well within the understanding of those of ordinary skill in the art and have not been disclosed in detail herein. These and other modifications and variations are well within the scope of the present disclosure and can be envisioned and implemented by those of ordinary skill in the art.

Moreover, while specific embodiments may have been illustrated and described collectively herein, it should be appreciated that any subsequent arrangement designed to achieve the same or similar purpose may be substituted for the specific embodiments described and/or shown herein. This disclosure is intended to cover any and all subsequent adaptations or variations of the various embodiments. Combinations of the above embodiments, and other embodiments not specifically described herein, will be apparent to those of ordinary skill in the art upon reviewing the present disclosure.

Other embodiments of the present disclosure will be apparent to those skilled in the art from consideration of the specification and practice of the embodiments disclosed herein. It is intended that the specification and examples be considered as exemplary only, and departure in form and detail may be made without departing from the scope and spirit of the present disclosure as defined by the following claims.

What is claimed is:

1. A device, comprising:
   a handle;
   a sheath coupled to the handle, the sheath including a lumen; and
   an instrument assembly coupled to the handle, and extending through the lumen of the sheath, the instrument assembly comprising:
      a basket movable relative to the sheath, and between contracted and expanded states, wherein the basket includes a plurality of struts, and wherein distal ends of the plurality of struts together form a common distal tip at the distal most end, and
      a forceps movable along a central axis of the basket and through an interior of the basket, and movable between closed and open states,
      wherein the forceps is movable between at least a first position within the basket and a second position outside of the basket by moving distally through a space or opening between at least two of the struts when the basket is in the contracted state and when the basket is in the expanded state.

2. The device of claim 1, wherein the forceps is configured to pass through the basket while the basket is in the expanded state.

3. The device of claim 1, wherein the forceps is configured to pass through the basket while the basket is contracted.

4. The device of claim 3, wherein in the contracted state of the basket, the basket includes a lumen configured to slidably receive the forceps.

5. The device of claim 1, wherein a central longitudinal axis of the forceps is coaxial with the central longitudinal axis of the basket when the basket is in the contracted state.

6. The device of claim 1, wherein the instrument assembly includes a forceps sheath, the forceps sheath including a forceps lumen configured to slidably receive the forceps.

7. The device of claim 6, wherein the forceps is extendable distally beyond the distal tip of the basket.

8. The device of claim 6, wherein the forceps is selectively retractable into and extendable out of the forceps lumen.

9. The device of claim 6, wherein the basket is at a distal portion of a basket sheath, the basket sheath including a forceps sheath lumen configured to slidably receive the forceps sheath.

10. A device, comprising:
    a handle;
    a first sheath coupled to and extending from a proximal end of the handle, the first sheath including a first lumen;
    an instrument assembly coupled to the handle, the instrument assembly comprising:
       a second sheath coupled to the handle and extending through the first lumen, the second sheath including a second lumen,
       a basket coupled to an end of the second sheath, the basket being movable relative to the first sheath, and between contracted and expanded states, wherein distal ends of struts of the basket together form a common distal tip in both the contracted and expanded states,
       a third sheath coupled to the handle and extending through the second lumen, the third sheath including a third lumen, the third sheath being movable relative to the second sheath, and between retracted and extended states, and
       a forceps coupled to the handle and extending through the third lumen, the forceps having an end effector movable relative to the third sheath, and between closed and open states.

11. The device of claim 10, wherein the first sheath includes a distal end opening, and the basket moves through the end opening when moving between the contracted and expanded states of the basket.

12. The device of claim 10, wherein longitudinal axes of portions of the first sheath, second sheath, third sheath, and forceps are coaxial.

13. The device of claim 10, wherein the forceps includes a proximal shaft and a plurality of distal arms, and wherein the forceps is movable between at least a first position within the basket and a second position outside of the basket by moving distally through a space or opening between at least two of the struts when the basket is in the contracted state and when the basket is in the expanded state.

14. The device of claim 10, wherein the handle assembly includes a housing, and a first slidable member configured to slide relative to the housing, a proximal portion of the second sheath being coupled to the first slidable member.

15. The device of claim 14, wherein the handle assembly includes a second slidable member configured to slide relative to the housing, a proximal portion of the third sheath being coupled to the second slidable member.

16. The device of claim 15, wherein the handle assembly includes a third slidable member configured to slide relative to the housing, a proximal portion of the forceps being coupled to the third slidable member.

17. The device of claim 16, wherein the second slidable member is configured to selectively engage with the third slidable member.

18. A method for handling an object in a target area of the body of a subject, comprising:
    positioning a distal end of a device at the target area, the device comprising:
       a handle,
       a sheath coupled to the handle, the sheath including a lumen, and
       an instrument assembly coupled to the handle, and extending through the lumen of the sheath, the instrument assembly comprising:
          a basket including a plurality of struts, wherein the basket is movable relative to the sheath and between contracted and expanded states, and wherein the distal ends of the struts of the basket together form a common distal tip in both the contracted and expanded states,
          a forceps including a plurality of distal arms movable along a central axis of the basket and through an interior of the basket, and movable between closed and open states, wherein the forceps is movable between at least a first position within the basket and a second position outside of the basket by moving distally through a space or opening between at least two of the struts when the basket is in the contracted state and when the basket is in the expanded state, and a forceps sheath coupled to the handle and movable relative to the handle and to the sheath, the forceps sheath including a forceps lumen, wherein the forceps and the distal arms are movable relative to the forceps sheath through the forceps lumen; and entrapping the object in an interior of the basket by moving the forceps from the first position to the second position through the basket and expanding and closing the forceps to grasp the object.

19. The method of claim 18, wherein entrapping the object in an interior of the basket includes extending the forceps between at least two struts of the basket and beyond a distal end of the basket to grasp the object, and retracting the forceps to draw the object into the interior of the basket.

20. The method of claim 19, further including extending the forceps to force the object back out of the interior of the basket, and releasing the forceps from the object outside of the basket.

\* \* \* \* \*